(12) United States Patent
Lee et al.

(10) Patent No.: US 9,115,289 B2
(45) Date of Patent: *Aug. 25, 2015

(54) MULTIBRANCHED BIOADHESIVE COMPOUNDS AND SYNTHETIC METHODS THEREFOR

(75) Inventors: Bruce P. Lee, Madison, WI (US); Sunil Silvary, Madison, WI (US); John L. Murphy, Verona, WI (US)

(73) Assignee: KENSEY NASH CORPORATION, Exton, PA (US)

( * ) Notice: Subject to any disclaimer, the term of this patent is extended or adjusted under 35 U.S.C. 154(b) by 223 days.

This patent is subject to a terminal disclaimer.

(21) Appl. No.: 13/148,286
(22) PCT Filed: Feb. 5, 2010
(86) PCT No.: PCT/US2010/023380
§ 371 (c)(1),
(2), (4) Date: Sep. 13, 2011
(87) PCT Pub. No.: WO2010/091298
PCT Pub. Date: Aug. 12, 2010

(65) Prior Publication Data
US 2012/0029559 A1   Feb. 2, 2012

Related U.S. Application Data

(60) Provisional application No. 61/150,479, filed on Feb. 6, 2009, provisional application No. 61/246,885, filed on Sep. 29, 2009.

(51) Int. Cl.
*A61L 15/18* (2006.01)
*A61L 15/58* (2006.01)
*C08G 63/664* (2006.01)
*C08G 69/44* (2006.01)
*G01N 29/036* (2006.01)
*C09D 5/16* (2006.01)
*C08G 73/10* (2006.01)

(52) U.S. Cl.
CPC ............... *C09D 5/1656* (2013.01); *A61L 15/18* (2013.01); *A61L 15/58* (2013.01); *C08G 63/664* (2013.01); *C08G 69/44* (2013.01); *C08G 73/1092* (2013.01)

(58) Field of Classification Search
CPC ...... A61L 15/18; A61L 15/58; C08G 63/664; C08G 69/44; C08G 73/1092; C09D 5/1656; G01N 2291/0256; G01N 29/036; G01N 33/54373; Y10S 436/827; Y10S 436/828; Y10S 436/829
USPC ................................ 424/78.17, 78.08, 78.28
See application file for complete search history.

(56) References Cited

U.S. PATENT DOCUMENTS

| RE38,827 E | 10/2005 | Barrows et al. |
| 7,342,077 B2 | 3/2008 | Ramesh |
| 2008/0087196 A1 | 4/2008 | Anderson et al. |
| 2008/0171836 A1* | 7/2008 | Lee ............................. 525/418 |
| 2008/0247984 A1* | 10/2008 | Messersmith et al. ..... 424/78.02 |
| 2008/0293910 A1 | 11/2008 | Kapiamba et al. |

FOREIGN PATENT DOCUMENTS

| WO | 2008/019352 | 2/2008 |
| WO | 2010/037045 | 4/2010 |

OTHER PUBLICATIONS

Luman et al., "Dendritic polymers composed of glycerol and succinic acid: Synthetic methodologies and medical applications", Pure Appl. Chem., 2004, vol. 76, Nos. 7, 8, pp. 1375-1385.

* cited by examiner

*Primary Examiner* — Ernst V Arnold
(74) *Attorney, Agent, or Firm* — Kirk J. Hogan; Casimir Jones, S.C.

(57) ABSTRACT

The invention describes new synthetic medical adhesives and antifouling coatings which exploit the key components of natural marine mussel adhesive proteins.

38 Claims, 23 Drawing Sheets

Medhesive-054

I(a)

Medhesive-096

I(b)

Medhesive-104

I(c)

Surphys-029

I(d)

Medhesive-105

I(e)

Medhesive-112

I(f)

Medhesive-116

I(g)

Bovine Paracardium Lap Shear Data for Trilayer Formulations

Schematic of multi-layer adhesive films.

Schematic of multi-layer adhesive films.

MULTIBRANCHED BIOADHESIVE COMPOUNDS AND SYNTHETIC METHODS THEREFOR

CROSS REFERENCE TO RELATED APPLICATIONS

This application claims priority to U.S. Provisional Patent Application Ser. No. 61/150,479 filed Feb. 6, 2009 and U.S. Provisional Patent Application Ser. No. 61/246,885 filed Sep. 29, 2009, each of which is herein incorporated by reference in its entirety.

REFERENCE TO FEDERAL FUNDING

The present application is a national phase application under 35 U.S.C. 0371 of PCT International Application No. PCT/US2010/023380, filed on Feb. 5, 2010, which claims priority to U.S. Provisional Patent Application Ser. No. 61/150,479 filed Feb. 6, 2009 and U.S. Provisional Patent Application Ser. No. 61/246,885 filed Sep. 29, 2009, each of which is herein incorporated by reference in its entirety. The government has certain rights in the invention.

FIELD OF THE INVENTION

The invention relates generally to new synthetic medical adhesives which exploit the key components of natural marine mussel adhesive proteins. The method exploits a biological strategy to modify surfaces that exhibit adhesive properties useful in a diverse array of medical applications. Specifically, the invention describes the use of peptides that mimic natural adhesive proteins in their composition and adhesive properties. These adhesive moieties are coupled to a polymer chain, and provide adhesive and crosslinking (cohesive properties) to the synthetic polymer.

BACKGROUND OF THE INVENTION

Mussel adhesive proteins (MAPs) are remarkable underwater adhesive materials secreted by certain marine organisms which form tenacious bonds to the substrates upon which they reside. During the process of attachment to a substrate, MAPs are secreted as adhesive fluid precursors that undergo a crosslinking or hardening reaction which leads to the formation of a solid adhesive plaque. One of the unique features of MAPs is the presence of L-3-4-dihydroxyphenylalanine (DOPA), an unusual amino acid which is believed to be responsible for adhesion to substrates through several mechanisms that are not yet fully understood. The observation that mussels adhere to a variety of surfaces in nature (metal, metal oxide, polymer) led to a hypothesis that DOPA-containing peptides can be employed as the key components of synthetic medical adhesives or coatings.

For example, bacterial attachment and biofilm formation are serious problems associated with the use of urinary stents and catheters as they often lead to chronic infections that cannot be resolved without removing the device. Although numerous strategies have been employed to prevent these events including the alteration of device surface properties, the application of anti-attachment and antibacterial coatings, host dietary and urinary modification, and the use of therapeutic antibiotics, no one approach has yet proved completely effective. This is largely due to three important factors, namely various bacterial attachment and antimicrobial resistance strategies, surface masking by host urinary and bacterial constituents, and biofilm formation. While the urinary tract has multiple anti-infective strategies for dealing with invading microorganisms, the presence of a foreign stent or catheter provides a novel, non-host surface to which they can attach and form a biofilm. This is supported by studies highlighting the ability of normally non-uropathogenic microorganisms to readily cause device-associated urinary tract infections. Ultimately, for a device to be clinically successful it must not only resist bacterial attachment but that of urinary constituents as well. Such a device would better allow the host immune system to respond to invading organisms and eradicate them from the urinary tract.

For example, bacterial attachment and subsequent infection and encrustation of uropathogenic *E. coli* (UPEC) cystitis is a serious condition associated with biofouling. Infections with *E. coli* comprise over half of all urinary tract device-associated infections, making it the most prevalent pathogen in such episodes.

Additionally, in the medical arena, few adhesives exist which provide both robust adhesion in a wet environment and suitable mechanical properties to be used as a tissue adhesive or sealant. For example, fibrin-based tissue sealants (e.g. Tisseel VH, Baxter Healthcare) provide a good mechanical match for natural tissue, but possess poor tissue-adhesion characteristics. Conversely, cyanoacrylate adhesives (e.g. Dermabond, ETHICON, Inc.) produce strong adhesive bonds with surfaces, but tend to be stiff and brittle in regard to mechanical properties and tend to release formaldehyde as they degrade.

Therefore, a need exists for materials that overcome one or more of the current disadvantages.

BRIEF SUMMARY OF THE INVENTION

The present invention surprisingly provides multi-armed, multihydroxy (dihydroxy)phenyl derivatives (DHPDs) having the general formula (I):

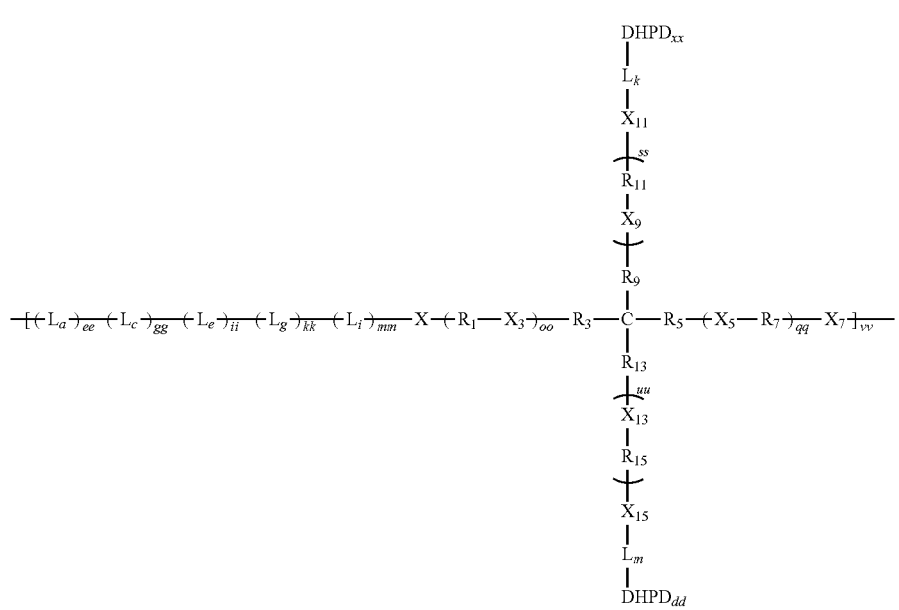

wherein each $L_a$, $L_c$, $L_e$, $L_g$ and $L_i$, independently, is a linker;

each $L_k$ and $L_m$, independently, is a linker or a suitable linking group selected from amine, amide, ether, ester, urea, carbonate or urethane linking groups;

each X, $X_3$, $X_5$, $X_7$, $X_9$, $X_{11}$, $X_{13}$ and $X_{15}$, independently, is an oxygen atom or NR;

R, if present, is H or a branched or unbranched C1-10 alkyl group;

each $R_1$, $R_3$, $R_5$, $R_7$, $R_9$, $R_{11}$, $R_{13}$ and $R_{15}$, independently, is a branched or unbranched C1-C15 alkyl group;

each $DHPD_{xx}$ and $DHPD_{dd}$, independently, is a multihydroxy phenyl derivative residue;

ee is a value from 1 to about 80;

gg is a value from 0 to about 80;

ii is a value from 0 to about 80;

kk is a value from 0 to about 80;

mm is a value from 0 to about 80;

oo is a value from 1 to about 120;

qq is a value from 1 to about 120;

ss is a value from 1 to about 120;

uu is a value from 1 to about 120; and vv is a value from 1 to about 80.

In one aspect, the compound of formula (I) $L_a$ is a residue of succinic acid; $L_c$ is a residue of a polycaprolactone or polylactic acid (thus forming an ester bond between terminal ends of the succinic acid and the hydroxyl oxygen of the ring opened lactone); $L_e$ is a residue of diethylene glycol (thus forming an ester bond between the ester portion of the lactone and one terminal hydroxyl group of the glycol); $L_g$ is a residue of a polycaprolactone or a polylactic acid (therefore forming an ester linkage between a second terminal end of a hydroxyl group of the glycol and the ring opened caprolactone); L is a residue of succinic acid or anhydride; X, $X_7$, $X_{11}$ and $X_{15}$ are each O or NH; $R_1$, $R_7$, $R_{11}$ and $R_{15}$ are each —$CH_2CH_2$— (thus forming a an amide or ester with the terminal end of an amine or hydroxyl terminated polyethylene glycol polyether); $X_3$, $X_5$, $X_9$ and $X_{13}$ are each O; $R_3$, $R_5$, $R_9$ and $R_{13}$ are each —$CH_2$—; $L_k$ and $L_m$ form an amide linkage between the terminal end of the DHPD and the respective X; and $DHPD_{xx}$ and $DHPD_{dd}$ are 3,4-dihydroxyhydrocinnamic acid (DOHA) residues.

In another aspect, $L_a$ is a residue of glycine; $L_c$ is a residue of a polycaprolactone or a polylactic acid; $L_e$ is a residue of diethylene glycol; $L_g$ is a residue of a polycaprolactone or a polylactic acid; $L_i$ is a residue of glycine; X, $X_7$, $X_{11}$ and $X_{15}$ are each O or NH; $R_1$, $R_7$, $R_{11}$ and $R_{15}$ are each —$CH_2CH_2$—; $X_3$, $X_5$, $X_9$ and $X_{13}$ are each O; $R_3$, $R_5$, $R_9$ and $R_{13}$ are each —$CH_2$—; $L_k$ and $L_m$ form a carbamate; and $DHPD_{xx}$ and $DHPD_{dd}$ are residues from 3,4 dihydroxyphenylethylamine.

In yet another aspect, $L_a$ is a residue of a poly(ethyleneglycol) bis(carboxymethyl)ether; $L_c$, $L_e$, $L_g$, and $L_i$ are absent; ee is a value from 1 to about 11; gg, ii, kk, and mm are each independently 0; X, $X_7$, $X_{11}$ and $X_{15}$ are each O or NH; $R_1$, $R_7$, $R_{11}$ and $R_{15}$ are each —$CH_2CH_2$—; $X_3$, $X_5$, $X_9$ and $X_{13}$ are each O; $R_3$, $R_5$, $R_9$ and $R_{13}$ are each —$CH_2$—; $L_k$ and $L_m$ form an amide; and $DHPD_{xx}$ and $DHPD_{dd}$ are residues from 3,4-dihydroxyhydrocinnamic acid (DOHA).

In still another aspect, FIG. 1 provides compounds I(a) through I(g) that depict certain embodiments of the invention.

Compound I(a), for example, has a Wt % DH (DOHA) of about 3.58+/−0.33%, Wt % PCL of about 12%, MW of about 97,650 g/mol with a PD of about 2.78.

Compound I(b), for example, has a Wt % DH of about 2.92+/−0.34%, Wt % PCL of about 20.7, MW of about 65,570 g/mol with a PD of about 4.414. MW's and PD were determined by gel permeation chromatography.

In one embodiment, the reaction products of the syntheses described herein are included as compounds or compositions useful as adhesives or surface treatment/antifouling aids. It should be understood that the reaction product(s) of the synthetic reactions can be purified by methods known in the art, such as diafiltration, chromatography, recrystallization/precipitation and the like or can be used without further purification.

In still another aspect, blends of the compounds of the invention described herein, can be prepared with various polymers. Polymers suitable for blending with the compounds of the invention are selected to impart non-covalent interactions with the compound(s), such as hydrophobic-hydrophobic interactions or hydrogen bonding with an oxygen atom on PEG and a substrate surface. These interactions can increase the cohesive properties of the film to a substrate. If a biopolymer is used, it can introduce specific bioactivity to the film, (i.e. biocompatibility, cell binding, immunogenicity, etc.).

Generally, there are four classes of polymers useful as blending agents with the compounds of the invention. Class 1 includes: Hydrophobic polymers (polyesters, PPG) with terminal functional groups (—OH, COOH, etc.), linear PCL-diols (MW 600-2000), branched PCL-triols (MW 900), wherein PCL can be replaced with PLA, PGA, PLAGA, and other polyesters.

Class 2 includes amphiphilic block (di, tri, or multiblock) copolymers of PEG and polyester or PPG, tri-block copolymers of PCL-PEG-PCL (PCL MW=500–3000, PEG MW=500=3000), tri-block copolymers of PLA-PEG-PLA (PCL MW=500=3000, PEG MW=500=3000). In other embodiments, PCL and PLA can be replaced with PGA, PLGA, and other polyesters. Pluronic polymers (triblock, diblock of various MW) and other PEG, PPG block copolymers are also suitable.

Class 3 includes hydrophilic polymers with multiple functional groups (—OH, —NH2, —COOH) along the polymeric backbone. These include, for example, PVA (MW 10,000-100,000), poly acrylates and poly methacrylates, and polyethylene imines.

Class 4 includes biopolymers such as polysaccharides, hyaluronic acid, chitosan, cellulose, or proteins, etc. which contain functional groups.

Abbreviations: PCL=polycaprolactone, PLA=polylactic acid, PGA=Polyglycolic acid, PLGA=a random copolymer of lactic and glycolic acid, PPG=polypropyl glycol, and PVA=polyvinyl alcohol.

It should be understood that the compounds of the invention can be coated multiple times to form bi, tri, etc. layers. The layers can be of the compounds of the invention per se, or of blends of a compound(s) and polymer, or combinations of a compound layer and a blend layer, etc.

Consequently, constructs can also include such layering of the compounds per se, blends thereof, and/or combinations of layers of a compound(s) per se and a blend or blends.

These adhesives of the invention described throughout the specification can be utilized for wound closure and materials of this type are often referred to as tissue sealants or surgical adhesives.

The compounds of the invention can be applied to a suitable substrate surface as a film or coating. Application of the compound(s) to the surface inhibits or reduces the growth of biofilm (bacteria) on the surface relative to an untreated substrate surface. In other embodiments, the compounds of the invention can be employed as an adhesive.

Exemplary applications include, but are not limited to fixation of synthetic (resorbable and non-resorbable) and biological membranes and meshes for hernia repair, void-eliminating adhesive for reduction of post-surgical seroma formation in general and cosmetic surgeries, fixation of synthetic (resorbable and non-resorbable) and biological membranes and meshes for tendon and ligament repair, sealing incisions after ophthalmic surgery, sealing of venous catheter access sites, bacterial barrier for percutaneous devices, as a contraceptive device, a bacterial barrier and/or drug depot for oral surgeries (e.g. tooth extraction, tonsillectomy, cleft palate, etc.), for articular cartilage repair, for antifouling or anti-bacterial adhesion.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1:
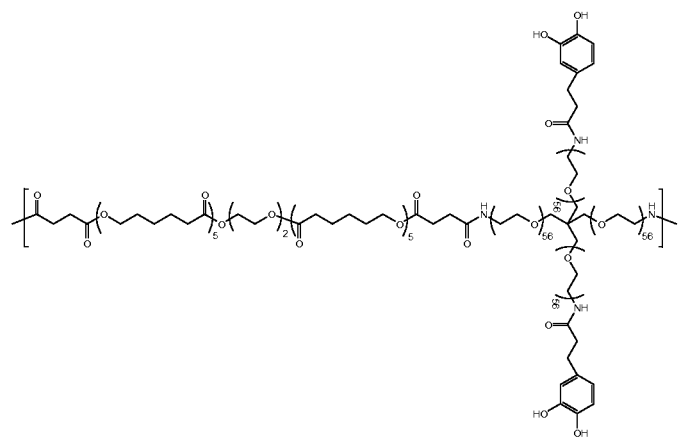
FIG. 1 provides compounds I(a) through I(g) as embodiments of the present invention.
Figure 1:
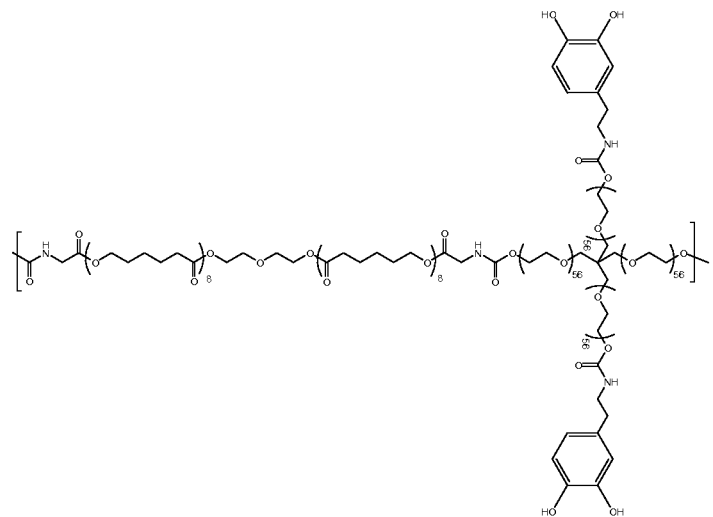
Figure 1:
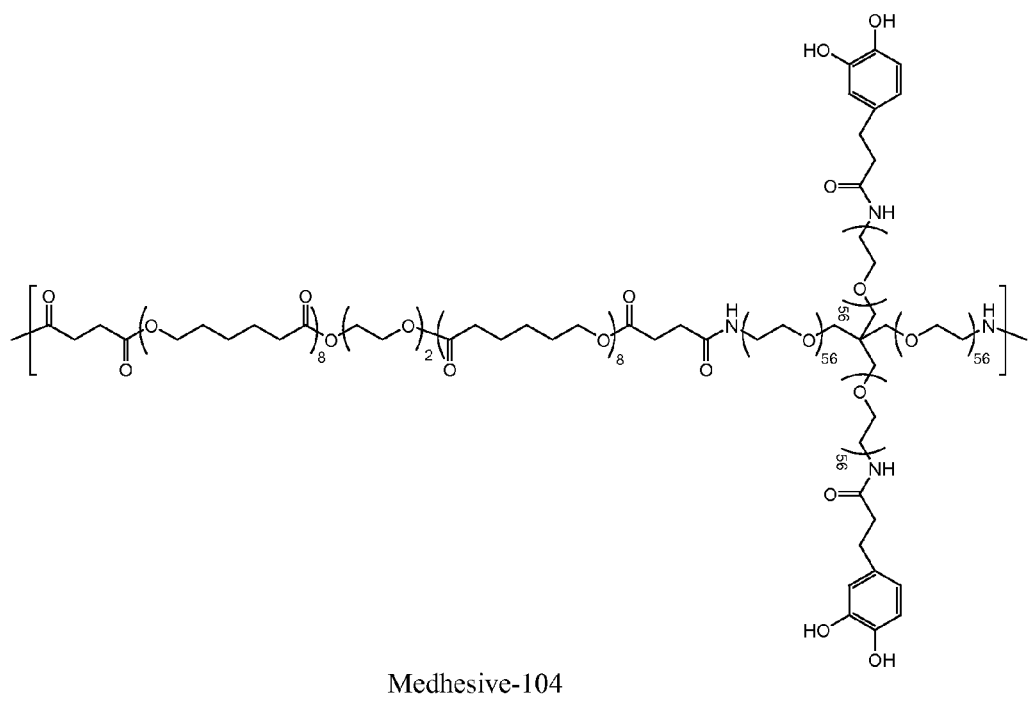
Figure 1:
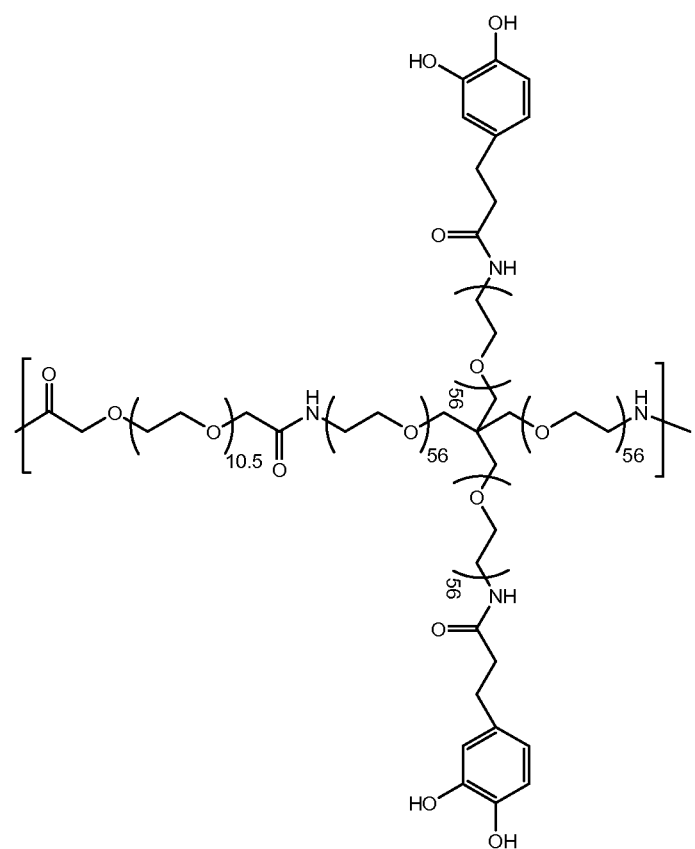
Figure 1:
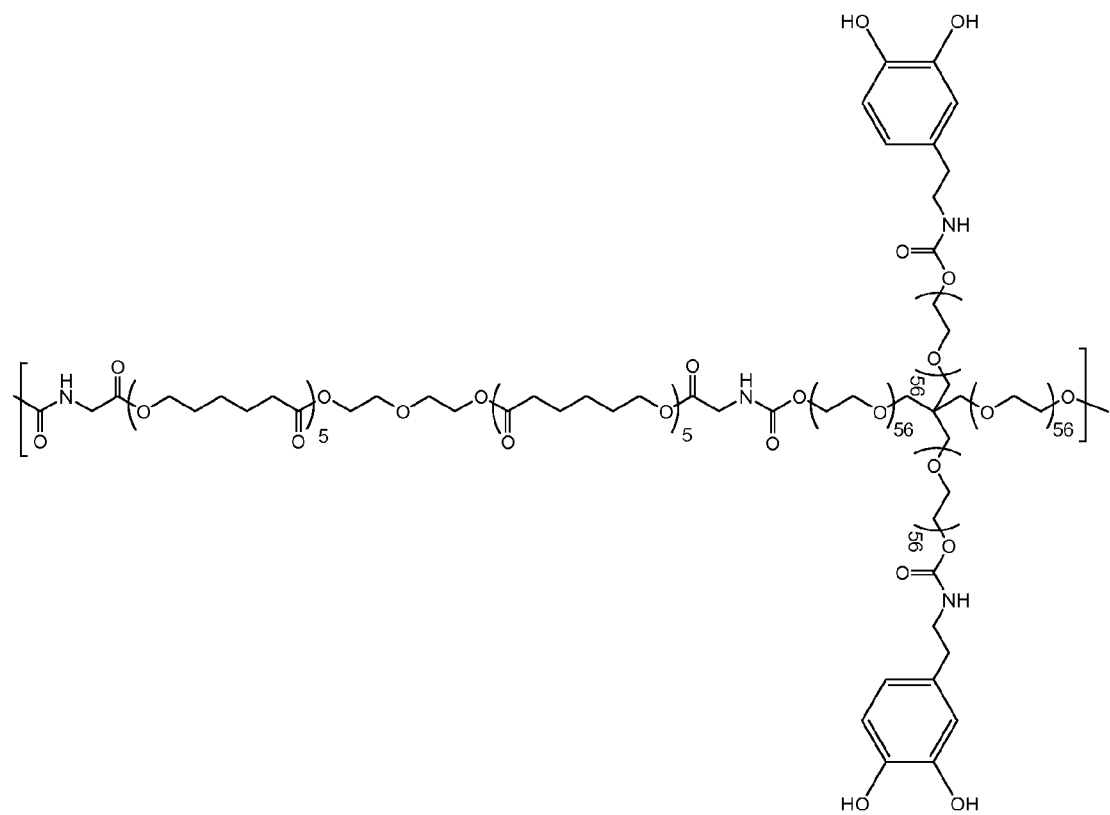
Figure 1:
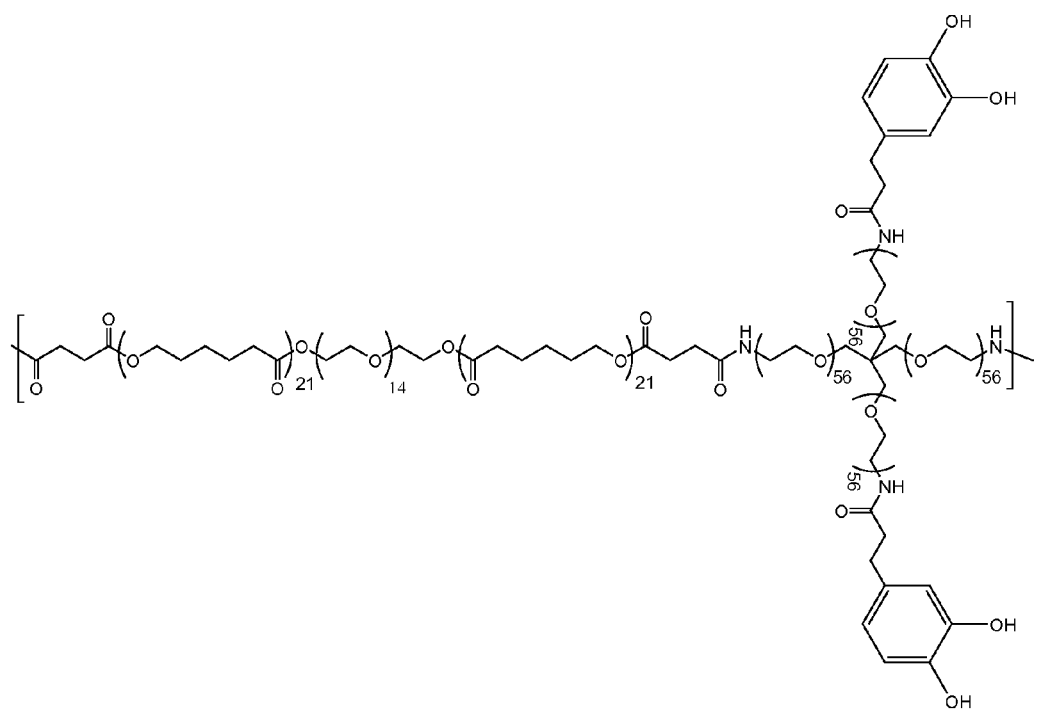
Figure 1:
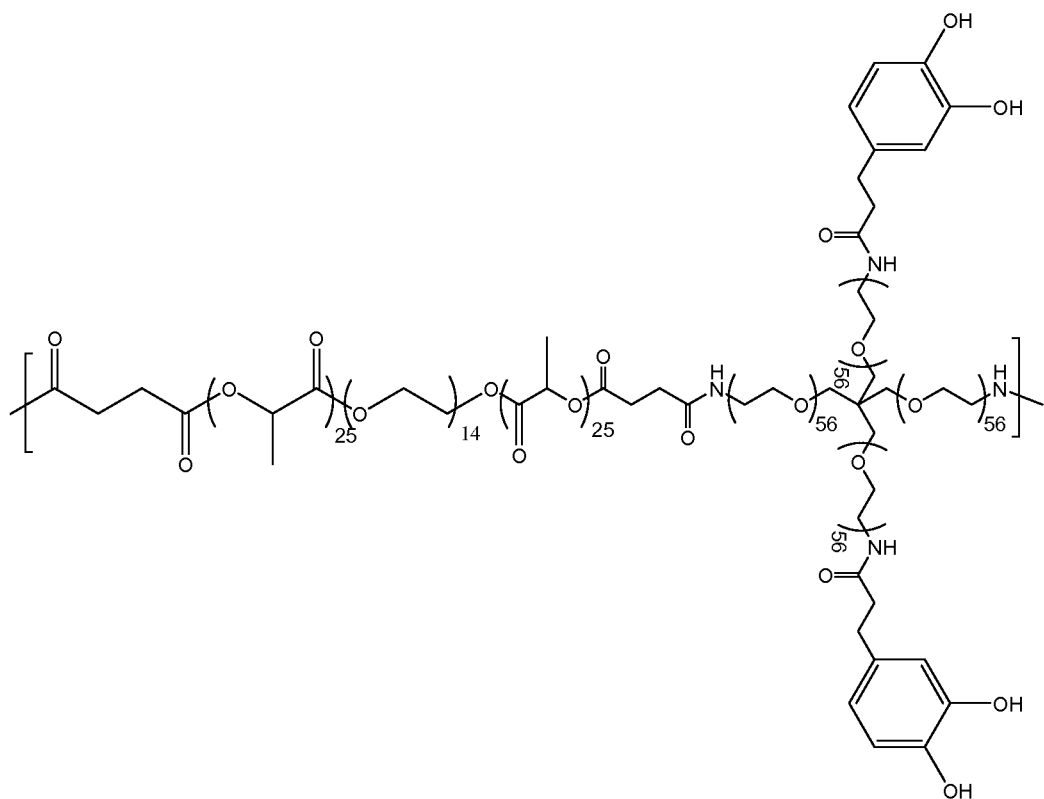

In the specification and in the claims, the terms "including" and "comprising" are open-ended terms and should be interpreted to mean "including, but not limited to . . . . " These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 15 carbon atoms ($C_1$-$C_{15}$ alkyl), more preferably from 1 to 10 carbon atoms ($C_1$-$C_{10}$ alkyl) and even more preferably from 1 to 6 carbon atoms ($C_1$-$C_6$ alkyl or lower alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkyldiyl" by itself or as part of another substituent refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group comprises from 1 to 6 carbon atoms (C1-C6 alkyldiyl). Also preferred are saturated acyclic alkanyldiyl groups in which the radical centers are at the terminal carbons, e.g., methandiyl (methano); ethan-1,2-diyl (ethano); propan-1,3- diyl (propano); butan-1,4-diyl (butano); and the like (also referred to as alkylenos, defined infra).

"Alkyleno," by itself or as part of another substituent, refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —OR", —SR", —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

The identifier "PA" refers to a poly(alkylene oxide) or substantially poly(alkylene oxide) and means predominantly or mostly alkyloxide or alkyl ether in composition. This definition contemplates the presence of heteroatoms e.g., N, O, S, P, etc. and of functional groups e.g., —COOH, —$NH_2$, —SH, or —OH as well as ethylenic or vinylic unsaturation. It is to be understood any such non-alkyleneoxide structures will only be present in such relative abundance as not to materially reduce, for example, the overall surfactant, non-toxicity, or immune response characteristics, as appropriate, of this polymer. It should also be understood that PAs can include terminal end groups such as PA-O—$CH_2$—$CH_2$—$NH_2$, e.g., PEG-O—$CH_2$—$CH_2$—$NH_2$ (as a common form of amine terminated PA). PA-O—$CH_2$—$CH_2$—$CH_2$—$NH_2$, e.g., PEG-O—$CH_2$—$CH_2$—$CH_2$—$NH_2$ is also available as well as PA-O—($CH_2$—$CH(CH_3)$—O)$_{xx}$—$CH_2$—$CH(CH_3)$—$NH_2$, where xx is 0 to about 3, e.g., PEG-O—($CH_2$—$CH(CH_3)$—O)$_{xx}$—$CH_2$—$CH(CH_3)$—$NH_2$ and a PA with an acid end-group typically has a structure of PA-O—$CH_2$—COOH, e.g., PEG-O—$CH_2$—COOH or PA-O—$CH_2$—$CH_2$—COOH, e.g., PEG-O—$CH_2$—$CH_2$—COOH. These can be considered "derivatives" of the PA. These are all contemplated as being within the scope of the invention and should not be considered limiting.

Suitable PAs (polyalkylene oxides) include polyethylene oxides (PEOs), polypropylene oxides (PPOs), polyethylene glycols (PEGs) and combinations thereof that are commercially available from SunBio Corporation, JenKem Technology USA, NOF America Corporation or Creative PEGWorks. It should be understood that, for example, polyethylene oxide can be produced by ring opening polymerization of ethylene oxide as is known in the art.

In one embodiment, the PA can be a block copolymer of a PEO and PPO or a PEG or a triblock copolymer of PEO/PPO/PEO.

Suitable MW ranges of the PA's are from about 300 to about 8,000 daltons, 400 to about 5,000 daltons or from about 450 to about 3,500 daltons.

It should be understood that the PA terminal end groups can be functionalized. Typically the end groups are OH, $NH_2$, COOH, or SH. However, these groups can be converted into a halide (Cl, Br, I), an activated leaving group, such as a tosylate or mesylate, an ester, an acyl halide, N-succinimidyl carbonate, 4-nitrophenyl carbonate, and chloroformate with the leaving group being N-hydroxy succinimide, 4-nitrophenol, and Cl, respectively. etc.

The notation of "L" refers to either a linker or a linking group. A "linker" refers to a moiety that has two points of attachment on either end of the moiety. For example, an alkyl dicarboxylic acid HOOC-alkyl-COOH (e.g., succinic acid) would "link" a terminal end group of a PA (such as a hydroxyl or an amine to form an ester or an amide respectively) with a reactive group of the DHPD (such as an $NH_2$, OH, or COOH). Suitable linkers include an acyclic hydrocarbon bridge (e.g, a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a monocyclic or polycyclic heteroaryl bridge (e.g., [3,4]furano [2,3]furano, pyridino, thiopheno, piperidino, piperazino, pyrazidino, pyrrolidino, and the like) or combinations of such bridges, dicarbonyl alkylenes, etc. Suitable dicarbonyl alkylenes include, C2 through C15 dicarbonyl alkylenes such as malonic acid, succinic acid, etc. Additionally, the anhydrides, acid halides and esters of such materials can be used to effect the linking when appropriate and can be considered "activated" dicarbonyl compounds.

Other suitable linkers include moieties that have two different functional groups that can react and link with an end group of a PA. These include groups such as amino acids (glycine, lysine, aspartic acid, etc.), PA's as described herein, poly(ethyleneglycol) bis(carboxymethyl)ethers, polyesters such as polylactides, lactones, polylactones such as polycaprolactone, lactams, polylactams such as polycaprolactam, polyglycolic acid (PGLA), moieties such as tyramine or dopamine and random or block copolymers of 2 or more types of polyesters.

Linkers further include compounds comprising the formula $Y_4$—$R_{17}$—C(=O)—$Y_6$, wherein $Y_4$ is OH, NHR, a halide, or an activated derivative of OH or NHR; $R_{17}$ is a branched or unbranched C1-C15 alkyl group; and $Y_6$ is NHR, a halide, or OR, wherein R is defined above. The term "activated derivative" refers to moieties that make the hydroxyl or amine more susceptible to nucleophilic displacement or for condensation to occur. For example, a hydroxyl group can be esterified by various reagents to provide a more active site for reaction to occur.

A linking group refers to the reaction product of the terminal end moieties of the PA and DHPD (the situation where "b" is 0; no linker present) condense to form an amide, ether, ester, urea, carbonate or urethane linkage depending on the reactive sites on the PA and DHPD. In other words, a direct bond is formed between the PA and DHPD portion of the molecule and no linker is present.

The term "residue" is used to mean that a portion of a first molecule reacts (e.g., condenses or is an addition product via a displacement reaction) with a portion of a second molecule to form, for example, a linking group, such an amide, ether, ester, urea, carbonate or urethane linkage depending on the reactive sites on the PA and DHPD. This can be referred to as "linkage".

The denotation "DHPD" refers to a multihydroxy phenyl derivative, such as a dihydroxy phenyl derivative, for example, a 3,4 dihydroxy phenyl moiety. Suitable DHPD derivatives include the formula:

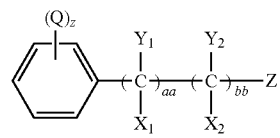

wherein Q is an OH;

"z" is 2 to 5;

each $X_1$, independently, is H, $NH_2$, OH, or COOH;

each $Y_1$, independently, is H, $NH_2$, OH, or COOH;

each $X_2$, independently, is H, $NH_2$, OH, or COOH;

each $Y_2$, independently, is H, $NH_2$, OH, or COOH;

Z is COOH, $NH_2$, OH or SH;

aa is a value of 0 to about 4;

bb is a value of 0 to about 4; and optionally provided that when one of the combinations of $X_1$ and $X_2$, $Y_1$ and $Y_2$, $X_1$ and $Y_2$ or $Y_1$ and $X_2$ are absent, then a double bond is formed between the $C_{aa}$ and $C_{bb}$, further provided that aa and bb are each at least 1.

In one aspect, z is 3.

In particular, "z" is 2 and the hydroxyls are located at the 3 and 4 positions of the phenyl ring.

In one embodiment, each $X_1$, $X_2$, $Y_1$ and $Y_2$ are hydrogen atoms, aa is 1, bb is 1 and Z is either COOH or $NH_2$.

In another embodiment, $X_1$ and $Y_2$ are both hydrogen atoms, $X_2$ is a hydrogen atom, aa is 1, bb is 1, $Y_2$ is $NH_2$ and Z is COOH.

In still another embodiment, $X_1$ and $Y_2$ are both hydrogen atoms, aa is 1, bb is 0, and Z is COOH or $NH_2$.

In still another embodiment, aa is 0, bb is 0 and Z is COOH or $NH_2$.

In still yet another embodiment, z is 3, aa is 0, bb is 0 and Z is COOH or $NH_2$.

It should be understood that where aa is 0 or bb is 0, then $X_1$ and $Y_1$ or $X_2$ and $Y_2$, respectively, are not present.

It should be understood, that upon condensation of the DHPD molecule with the PA that a molecule of water, for example, is generated such that a bond is formed as described above (amide, ether, ester, urea, carbonate or urethane).

In particular, DHPD molecules include 3,4-dihydroxyphenethylamine (dopamine), 3,4-dihydroxy phenylalanine (DOPA), 3,4-dihydroxyhydrocinnamic acid, 3,4-dihydroxyphenyl ethanol, 3,4 dihydroxyphenylacetic acid, 3,4 dihydroxyphenylamine, 3,4-dihydroxybenzoic acid, etc.

The present invention surprisingly provides multi-armed, multihydroxy (dihydroxy)phenyl derivatives (DHPDs) having the general formula:

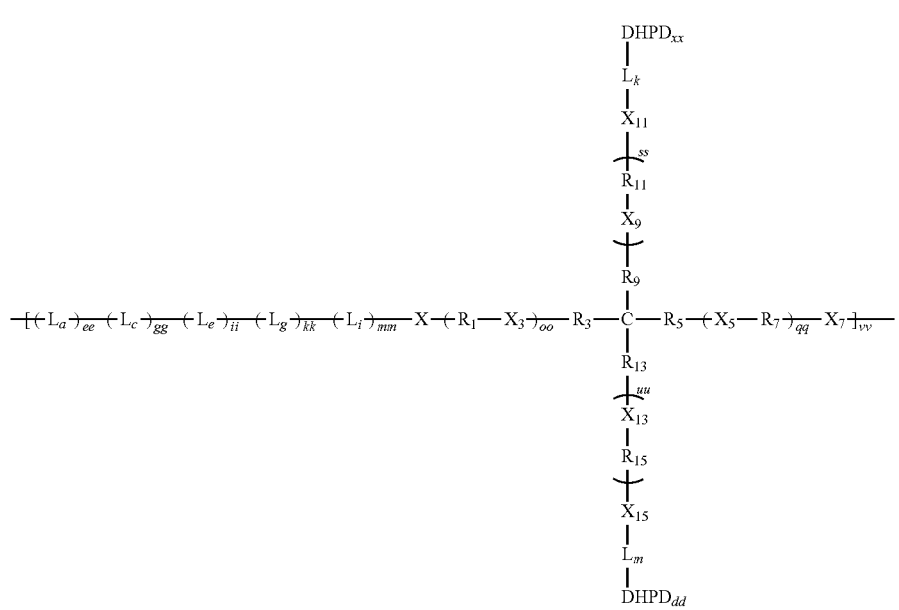

wherein each $L_a$, $L_c$, $L_e$, $L_g$ and $L_i$, independently, is a linker;

each $L_k$ and $L_m$, independently, is a linker or a suitable linking group selected from amine, amide, ether, ester, urea, carbonate or urethane linking groups;

each X, $X_3$, $X_5$, $X_7$, $X_9$, $X_{11}$, $X_{13}$ and $X_{15}$, independently, is an oxygen atom or NR;

R, if present, is H or a branched or unbranched C1-10 alkyl group;

each $R_1$, $R_3$, $R_5$, $R_7$, $R_9$, $R_{11}$, $R_{13}$ and $R_{15}$, independently, is a branched or unbranched C1-C15 alkyl group;

each $DHPD_{xx}$ and $DHPD_{dd}$, independently, is a multihydroxy phenyl derivative residue;

ee is a value from 1 to about 80, in particular from 1 to about 50, more particularly, from 1 to about 20, and more particularly from 1 to about 10;

gg is a value from 0 to about 80, in particular from 1 to about 50, more particularly, from 1 to about 25, and more particularly from 1 to about 10;

ii is a value from 0 to about 80, in particular from 1 to about 50, more particularly, from 1 to about 25, and more particularly from 1 to about 15;

kk is a value from 0 to about 80, in particular from 1 to about 50, more particularly, from 1 to about 25, and more particularly from 1 to about 10;

mm is a value from 0 to about 80, in particular from 1 to about 50, more particularly, from 1 to about 20, and more particularly from 1 to about 10;

oo is a value from 1 to about 120, in particular from 1 to about 60, more particularly from 1 to about 30, and more particularly from 1 to about 10;

qq is a value from 1 to about 120, in particular from 1 to about 60, more particularly from 1 to about 30, and more particularly from 1 to about 10;

ss is a value from 1 to about 120, in particular from 1 to about 60, more particularly from 1 to about 30, and more particularly from 1 to about 10;

uu is a value from 1 to about 120, in particular from 1 to about 60, more particularly from 1 to about 30, and more particularly from 1 to about 10; and vv is a value from 1 to about 80, in particular from 1 to about 50, more particularly, from 1 to about 20, and more particularly from 1 to about 10.

In one example, oo, qq, ss and uu are all about equal or equal.

For example, each $L_a$, $L_c$, $L_e$, $L_g$ and L, independently if present, is a linker selected from the residue of a C1-C15 alkyl anhydride or activated dicarbonyl moiety, a polyethylene glycol, a poly(ethyleneglycol) bis(carboxymethyl)ether, an amino acid, a C1-C15 alkyl lactone or lactam, a poly C1-C15 alkyl lactone or lactam, a polyester, a compound comprising the formula $Y_4$—$R_{17}$—C(=O)—$Y_6$, wherein $Y_4$ is OH, NHR, a halide, or an activated derivative of OH or NHR; $R_{17}$ is a branched or unbranched C1-C15 alkyl group; and $Y_6$ is NHR, a halide, or OR, wherein R is as described above, a residue of an C1-C15 alkylene diol, a C1-C15 alkylene diamine, a poly(alkylene oxide) polyether or derivative thereof or —O—$CH_2CH_2$—O—$CH_2CH_2$—O—.

In certain embodiments, $L_a$, when present, is a residue of a C1-C15, alkyl anhydride or activated dicarbonyl moiety, a poly(ethyleneglycol) bis(carboxymethyl)ether or an amino acid, wherein the activated dicarbonyl moiety is a residue of succinic acid or the amino acid is glycine.

In certain embodiments, $L_c$, when present, is a residue of a C1-C15 alkyl lactone or lactam, a poly C1-C15 alkyl lactone or lactam, a polyester, or a compound comprising the formula $Y_4$—$R_{17}$—C(=O)—$Y_6$, wherein $Y_4$ is OH, NHR, a halide, or an activated derivative of OH or NHR; $R_{17}$ is a branched or unbranched C1-C15 alkyl group; and $Y_6$ is NHR, a halide, or OR, wherein R is as described above. In particular, the polylactone is a polycaprolactone or the polyester is a polylactide (polylactic acid).

In certain embodiments, $L_e$, when present, is a residue of an alkylene diol, such as a polyethylene glycol, an alkylene diamine or a poly(alkylene oxide) polyether or derivative thereof. In particular, $L_e$ is a poly(alkylene oxide) or —O—$CH_2CH_2$—O—$CH_2CH_2$—O—.

In certain embodiments, $L_g$, when present, is a residue of a C1-C15 alkyl lactone or lactam, a poly C1-C15 alkyl lactone or lactam, or a compound comprising the formula $Y_4$—$R_{17}$—

C(=O)—Y$_6$, wherein Y$_4$ is OH, NHR, a halide, or an activated derivative of OH or NHR; R$_{17}$ is a branched or unbranched C1-C15 alkyl group; and Y$_6$ is NHR, a halide, or OR, where R is described above. In particular, the polylactone is a polycaprolactone or the polyester is a polylactide (polylactic acid).

In certain embodiments, L$_{tj}$, when present, is a residue of a C1-C15 alkyl anhydride or activated dicarbonyl moiety, a poly(ethyleneglycol) bis(carboxymethyl)ether or an amino acid, wherein the activated dicarbonyl moiety is a residue of succinic acid or the amino acid is glycine.

In certain embodiments, X, X$_7$, X$_{11}$ and X$_{15}$ are each O or NH.

In certain embodiments, R$_1$, R$_7$, R$_{11}$ and R$_{15}$ are each —CH$_2$CH$_2$—

In certain embodiments, X$_3$, X$_5$, X$_9$ and X$_{13}$ are each O.

In certain embodiments, R$_3$, R$_5$, R$_9$ and R$_{13}$ are each —CH$_2$—.

In certain embodiments, L$_k$ and L$_m$ form/are an amide, ester or carbamate.

In certain embodiments, L$_a$ as a residue of a poly(ethyleneglycol) bis(carboxymethyl)ether is not included as a linker.

It should be understood that a person having ordinary skill in the art would select appropriate combinations of linkers to provide an array of condensation products embodied and described herein.

In certain embodiments an oxidant is included with the bioadhesive film layer. The oxidant can be incorporated into the polymer film or it can be contacted to the film at a later time. A solution could be sprayed or brushed onto either the adhesive surface or the tissue substrate surface. Alternatively, the construct can be dipped or submerged in a solution of oxidant prior to contacting the tissue substrate. In any situation, the oxidant upon activation, can help promote crosslinking of the multihydroxy phenyl groups with each other and/or tissue. Suitable oxidants include periodates and the like.

The invention further provides crosslinked bioadhesive constructs or hydrogels derived from the compositions described herein. For example, two DHDP moieties from two separate polymer chains can be reacted to form a bond between the two DHDP moieties. Typically, this is an oxidative/radical initiated crosslinking reaction wherein oxidants/initiators such as NaIO$_3$, NaIO$_4$, Fe III salts, (FeCl$_3$), Mn III salts (MnCl$_3$), H$_2$O$_2$, oxygen, an inorganic base, an organic base or an enzymatic oxidase can be used. Typically, a ratio of oxidant/initiator to DHDP containing material is between about 0.2 to about 1.0 (on a molar basis) (oxidant:DHDP). In one particular embodiment, the ratio is between about 0.25 to about 0.75 and more particularly between about 0.4 to about 0.6 (e.g., 0.5). It has been found that periodate is very effective in the preparation of crosslinked hydrogels of the invention. Additionally, it is possible that oxidation "activates" the DHPD(s) which allow it to form interfacial crosslinking with appropriate surfaces with functional group (i.e. biological tissues with —NH$_2$, —SH, etc.)

The compositions of the invention can be utilized by themselves or in combination with polymers to form a blend. Suitable polymers include, for example, polyesters, PPG, linear PCL-diols (MW 600-2000), branched PCL-triols (MW 900), wherein PCL can be replaced with PLA, PGA, PLGA, and other polyesters, amphiphilic block (di, tri, or multiblock) copolymers of PEG and polyester or PPG, tri-block copolymers of PCL-PEG-PCL (PCL MW=500=3000, PEG MW=500=3000), tri-block copolymers of PLA-PEG-PLA (PCL MW=500=3000, PEG MW=500–3000), wherein PCL and PLA can be replaced with PGA, PLGA, and other polyesters. Pluronic polymers (triblock, diblock of various MW) and other PEG, PPG block copolymers are also suitable. Hydrophilic polymers with multiple functional groups (—OH, —NH$_2$, —COOH) contained within the polymeric backbone such as PVA (MW 10,000-100,000), poly acrylates and poly methacrylates, polyvinylpyrrolidone, and polyethylene imines are also suitable. Biopolymers such as polysaccharides (e.g., dextran), hyaluronic acid, chitosan, gelatin, cellulose (e.g., carboxymethyl cellulose), proteins, etc. which contain functional groups can also be utilized.

Abbreviations: PCL=polycaprolactone, PLA=polylactic acid, PGA=Polyglycolic acid, PLGA=a random copolymer of lactic and glycolic acid, PPG=polypropyl glycol, and PVA=polyvinyl alcohol.

Typically, blends of the invention include from about 0 to about 99.9% percent (by weight) of polymer to composition(s) of the invention, more particularly from about 1 to about 50 and even more particularly from about 1 to about 30.

The compositions of the invention, either a blend or a compound of the invention per se, can be applied to suitable substrates using conventional techniques. Coating, dipping, spraying, spreading and solvent casting are possible approaches.

In one embodiment, adhesive compounds of the present invention provide a method of adhering a first surface to a second surface in a subject. In some embodiments, the first and second surfaces are tissue surfaces, for example, a natural tissue, a transplant tissue, or an engineered tissue. In further embodiments, at least one of the first and second surfaces is an artificial surface. In some embodiments, the artificial surface is an artificial tissue. In other embodiments, the artificial surface is a device or an instrument. In some embodiments, adhesive compounds of the present invention seal a defect between a first and second surface in a subject. In other embodiments, adhesive compounds of the present invention provide a barrier to, for example, microbial contamination, infection, chemical or drug exposure, inflammation, or metastasis. In further embodiments, adhesive compounds of the present invention stabilize the physical orientation of a first surface with respect to a second surface. In still further embodiments, adhesive compounds of the present invention reinforce the integrity of a first and second surface achieved by, for example, sutures, staples, mechanical fixators, or mesh. In some embodiments, adhesive compounds of the present invention provide control of bleeding. In other embodiments, adhesive compounds of the present invention provide delivery of drugs including, for example, drugs to control bleeding, treat infection or malignancy, or promote tissue regeneration.

The present invention surprisingly provides unique bioadhesive constructs that are suitable to repair or reinforce damaged tissue.

The present invention also surprisingly provides unique antifouling coatings/constructs that are suitable for application in, for example, urinary applications. The coatings could be used anywhere that a reduction in bacterial attachment is desired: dental unit waterlines, implantable orthopedic devices, cardiovascular devices, wound dressings, percutaneous devices, surgical instruments, marine applications, food preparation surfaces and utensils.

The constructs include a suitable support that can be formed from a natural material, such as collagen, pericardium, dermal tissues, small intestinal submucosa or man made materials such as polypropylene, polyethylene, polybutylene, polyesters, PTFE, PVC, polyurethanes and the like. The support can be a film, a membrane, a mesh, a non-woven and the like. The support need only help provide a surface for the bioadhesive to adhere. The support should also help facilitate physiological reformation of the tissue at the damaged site. Thus the constructs of the invention provide a site for remodeling via fibroblast migration, followed by subsequent native collagen deposition. For biodegradable support of either biological or synthetic origins, degradation of the support and the adhesive can result in the replacement of the bioadhesive construct by the natural tissues of the patient.

The constructs of the invention can include a compound of the invention or mixtures thereof or a blend of a polymer with one or more of the compounds of the invention. In one embodiment, the construct is a combination of a substrate, to which a blend is applied, followed by a layer(s) of one or more compounds of the invention.

In another embodiment, two or more layers can be applied to a substrate wherein the layering can be combinations of one or more blends or one or more compositions of the invention. The layering can alternate between a blend and a composition layer or can be a series of blends followed by a composition layer or vice versa.

Not to be limited by theory, it is believe that to improve the overall adhesive strength of the present adhesives, two separate properties require consideration: 1) interfacial binding ability or "adhesion" to a substrate and 2) bulk mechanical properties or "cohesion". It is possible that some polymers may generally fail cohesively, meaning that their adhesive properties are better than their cohesive properties. That is one basis why blending with a hydrophobic polymer increases the bulk cohesive properties. For example, an increase in the overall adhesive strength (FIG. 4) was found and we also a change in the mode of failure mode was also noted. For example, at the highest PCL content (30%), the blend failed adhesively, which supports the hypothesis that blending of PCL increases cohesive properties.

It has interestingly been found that use of a blend advantageously has improved adhesion to the substrate surface. For example, a blend of a hydrophobic polymer with a composition of the invention of Formula (I) has improved overall cohesive properties of Formula (I) and thus the overall strength of the adhesive joint. Subsequent application of a composition of Formula I to the blend layer then provides improved interfacial adhesion between the blend and provides for improved adhesive properties to the tissue to be adhered to as the hydrophobic polymer is not in the outermost layer.

Typically the loading density of the coating layer is from about 0.001 g/m² to about 200 g/m², more particularly from about 5 g/m² to about 150 g/m², and more particularly from about 10 g/m² to about 100 g/m². Thus, typically a coating has a thickness of from about 1 to about 200 nm. More typically for an adhesive, the thickness of the film is from about 1 to about 200 microns.

The following paragraphs enumerated consecutively from 1 through 37 provide for various aspects of the present invention. In one embodiment, in a first paragraph (1), the present invention provides a compound comprising the formula (I)

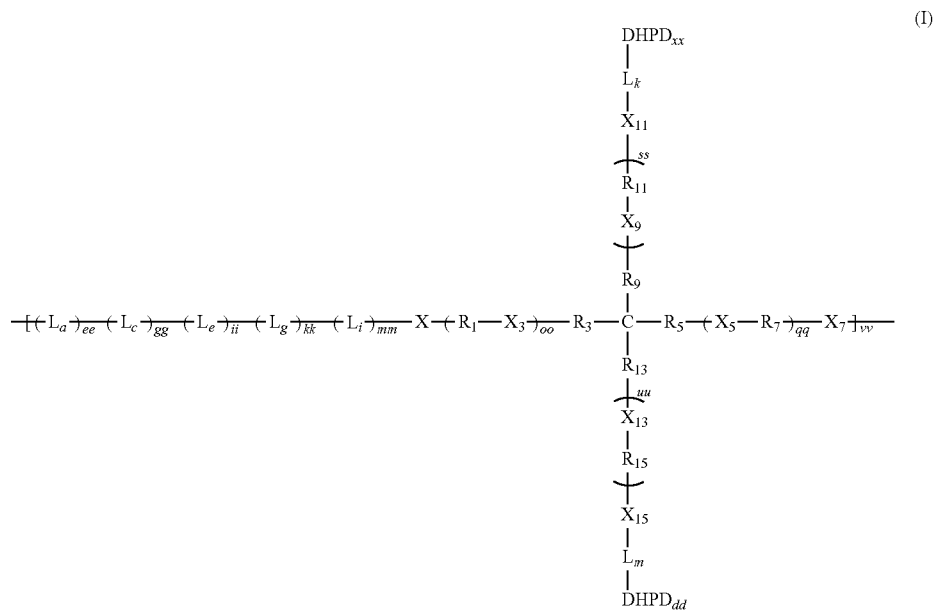

wherein each $L_a$, $L_c$, $L_e$, $L_g$ and $L_i$, independently, is a linker;

each $L_k$ and $L_m$, independently, is a linker or a suitable linking group selected from amine, amide, ether, ester, urea, carbonate or urethane linking groups;

each X, $X_3$, $X_5$, $X_7$, $X_9$, $X_{11}$, $X_{13}$ and $X_{15}$, independently, is an oxygen atom or NR;

R, if present, is H or a branched or unbranched C1-10 alkyl group;

each $R_1$, $R_3$, $R_5$, $R_7$, $R_9$, $R_{11}$, $R_{13}$ and $R_{15}$, independently, is a branched or unbranched C1-C15 alkyl group;

each $DHPD_{xx}$ and $DHPD_{dd}$, independently, is a multihydroxy phenyl derivative residue;

ee is a value from 1 to about 80;
gg is a value from 0 to about 80:
ii is a value from 0 to about 80;
kk is a value from 0 to about 80;
mm is a value from 0 to about 80;
oo is a value from 1 to about 120;
qq is a value from 1 to about 120;
ss is a value from 1 to about 120;
uu is a value from 1 to about 120; and
vv is a value from 1 to about 80.

2. The compound of paragraph 1, wherein $L_a$ is a residue of a C1-C15, alkyl anhydride or activated dicarbonyl moiety, a poly(ethyleneglycol) bis(carboxymethyl)ether, polyethylene glycol or an amino acid.

3. The compound of paragraph 2, wherein the dicarbonyl moiety is a residue of succinic acid or the amino acid is glycine.

4. The compound of any of paragraphs 1 through 3, wherein $L_c$ is a residue of a C1-C15 alkyl lactone or lactam, a poly C1-C15 alkyl lactone or lactam, a polyester, or a compound comprising the formula $Y_4$—$R_{17}$—C(=O)—$Y_6$,
wherein $Y_4$ is OH, NHR, a halide, or an activated derivative of OH or NHR;
$R_{17}$ is a branched or unbranched C1-C15 alkyl group; and
$Y_6$ is NHR, a halide, or OR.

5. The compound of paragraph 4, wherein the polylactone is a polycaprolactone.

6. The compound of any of paragraphs 1 through 5,
wherein $L_e$ is a residue of an alkylene diol, an alkylene diamine or a poly(alkylene oxide) polyether or derivative thereof.

7. The compound of paragraph 6, wherein $L_e$ is a poly (alkylene oxide) or —O—$CH_2CH_2$—O—$CH_2CH_2$—O—.

8. The compound of any of paragraphs 1 through 7, wherein $L_g$ is a residue of a C1-C15 alkyl lactone or lactam, a poly C1-C15 alkyl lactone or lactam, or a compound comprising the formula $Y_4$—$R_{17}$—C(=O)—$Y_6$,
wherein $Y_4$ is OH, NHR, a halide, or an activated derivative of OH or NHR;
$R_{17}$ is a branched or unbranched C1-C15 alkyl group; and
$Y_6$ is NHR, a halide, or OR.

9. The compound of paragraph 8, wherein the polylactone is polycaprolactone.

10. The compound of any of paragraphs 1 through 9, wherein $L_i$ is a residue of a C1-C15 alkyl anhydride or activated dicarbonyl moiety, a poly(ethyleneglycol) bis(carboxymethyl)ether or an amino acid.

11. The compound of paragraph 10, wherein $L_i$ is a residue of succinic acid or glycine.

12. The compound of any of paragraphs 1 through 11, wherein X, $X_7$, $X_{11}$ and $X_{15}$ are each O or NH.

13. The compound of any of paragraphs 1 through 12, wherein $R_1$, $R_7$, $R_{11}$ and $R_{15}$ are each —$CH_2CH_2$—.

14. The compound of any of paragraphs 1 through 13, wherein $X_3$, $X_5$, $X_9$ and $X_{13}$ are each O.

15. The compound of any of paragraphs 1 through 14, wherein $R_3$, $R_5$, $R_9$ and $R_{13}$ are each —$CH_2$—.

16. The compound of any of paragraphs 1 through 15, wherein $L_k$ and $L_m$ form an amide, ester or carbamate.

17. The compound of any of paragraphs 1 through 16, wherein each $DHPD_{xx}$ and $DHPD_{dd}$, independently, is a residue of a formula comprising:

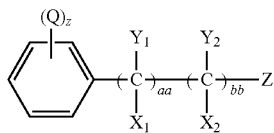

wherein Q is an OH;
"z" is 2 to 5;
each $X_1$, independently, is H, $NH_2$, OH, or COOH;
each $Y_1$, independently, is H, $NH_2$, OH, or COOH;
each $X_2$, independently, is H, $NH_2$, OH, or COOH;
each $Y_2$, independently, is H, $NH_2$, OH, or COOH;

Z is COOH, $NH_2$, OH or SH;
aa is a value of 0 to about 4;
bb is a value of 0 to about 4; and
optionally provided that when one of the combinations of $X_1$ and $X_2$, $Y_1$ and $Y_2$, $X_1$ and $Y_2$ or $Y_1$ and $X_2$ are absent, then a double bond is formed between the $C_{aa}$ and $C_{bb}$, further provided that aa and bb are each at least 1 to form the double bond when present.

18. The compound of any of paragraphs 1 through 17, wherein $DHPD_{xx}$ and $DHPD_{dd}$ residues are from 3,4-dihydroxy phenylalanine (DOPA), 3,4-dihydroxyhydrocinnamic acid (DOHA), 3,4-dihydroxyphenyl ethanol, 3,4 dihydroxyphenylacetic acid, 3,4 dihydroxyphenylamine, or 3,4-dihydroxybenzoic acid.

19. The compound of paragraph 1, wherein
$L_a$ is a residue of succinic acid;
$L_c$ is a residue of a polycaprolactone, a caprolactone, a polylactic acid, a polylactone or a lactic acid or lactone;
$L_e$ is a residue of a polyethylene glycol, e.g., diethylene glycol;
$L_g$ is a residue of a polycaprolactone, a caprolactone, a polylactic acid, a polylactone or a lactic acid or lactone;
$L_i$ is a residue of succinic anhydride;
X, $X_7$, $X_{11}$ and $X_{15}$ are each O or NH;
$R_1$, $R_7$, $R_{11}$ and $R_{15}$ are each —$CH_2CH_2$—;
$X_3$, $X_5$, $X_9$ and $X_{13}$ are each O;
$R_3$, $R_5$, $R_9$ and $R_{13}$ are each —$CH_2$—;
$L_k$ and $L_m$ form an amide; and
$DHPD_{xx}$ and $DHPD_{dd}$ are residues from 3,4-dihydroxyhydrocinnamic acid (DOHA).

20. The compound of paragraph 1, wherein
$L_a$ is a residue of glycine;
$L_c$ is a residue of a polycaprolactone;
$L_e$ is a residue of a polyethylene glycol, e.g., diethylene glycol;
$L_g$ is a residue of a polycaprolactone;
$L_i$ is a residue of glycine;
X, $X_7$, $X_{11}$ and $X_{15}$ are each O or NH;
$R_1$, $R_7$, $R_{11}$ and $R_{15}$ are each —$CH_2CH_2$—;
$X_3$, $X_5$, $X_9$ and $X_{13}$ are each O;
$R_3$, $R_5$, $R_9$ and $R_{13}$ are each —$CH_2$—;
$L_k$ and $L_m$ form a carbamate; and
$DHPD_{xx}$ and $DHPD_{dd}$ are residues from 3,4 dihydroxyphenylethylamine.

21. The compound of paragraph 1, wherein
$L_a$ is a residue of a poly(ethyleneglycol) bis(carboxymethyl)ether;
$L_c$, $L_e$, $L_g$, and $L_i$ are absent;
ee is a value from 1 to about 11;
gg, ii, kk, and mm are each independently 0;
X, $X_7$, $X_{11}$ and $X_{15}$ are each O or NH;
$R_1$, $R_7$, $R_{11}$ and $R_{15}$ are each —$CH_2CH_2$—;
$X_3$, $X_5$, $X_9$ and $X_{13}$ are each O;
$R_3$, $R_5$, $R_9$ and $R_{13}$ are each —$CH_2$—;
$L_k$ and $L_m$ form an amide; and
$DHPD_{xx}$ and $DHPD_{dd}$ are residues from 3,4-dihydroxyhydrocinnamic acid (DOHA).

22. A bioadhesive construct, comprising:
a support suitable for tissue repair or reconstruction; and
a coating comprising a multihydroxyphenyl (DHPD) functionalized polymer (DHPp) of any of paragraphs 1 through 21.

23. The bioadhesive construct of paragraph 22, further comprising an oxidant.

24. The bioadhesive construct of either of paragraphs 22 or 23, wherein the oxidant is formulated with the coating.

25. The bioadhesive construct of either of paragraphs 22 or 23, wherein the oxidant is applied to the coating.

26. The bioadhesive construct of any of paragraphs 22 through 25, wherein the support is a film, a mesh, a membrane, a nonwoven or a prosthetic.

27. A blend of a polymer and a compound of any of paragraphs 1 through 21.

28. The blend of paragraph 27, wherein the polymer is present in a range of about 1 to about 50 percent by weight.

29. The blend of paragraph 28, wherein the polymer is present in a range of about 1 to about 30 percent by weight.

30. A bioadhesive construct comprising:
a support suitable for tissue repair or reconstruction; and
a coating comprising any of the blends of paragraphs 27 through 29.

31. The bioadhesive construct of paragraph 30, further comprising an oxidant.

32. The bioadhesive construct of either of paragraphs 30 or 31, wherein the oxidant is formulated with the coating.

33. The bioadhesive construct of either of paragraphs 30 or 31, wherein the oxidant is applied to the coating.

34. The bioadhesive construct of any of paragraphs 30 through 33, wherein the support is a film, a mesh, a membrane, a nonwoven or a prosthetic.

35. A bioadhesive construct comprising:
a support suitable for tissue repair or reconstruction;
a first coating comprising a multihydroxyphenyl (DHPD) functionalized polymer (DHPp) of any of paragraphs 1 through 21 and a polymer; and
a second coating coated onto the first coating, wherein the second coating comprises a multihydroxyphenyl (DHPD) functionalized polymer (DHPp) of any of paragraphs 1 through 21.

36. A bioadhesive construct comprising:
a support suitable for tissue repair or reconstruction;
a first coating comprising a first multihydroxyphenyl (DHPD) functionalized polymer (DHPp) of any of paragraphs 1 through 21 and a first polymer; and
a second coating coated onto the first coating, wherein the second coating comprises a second multihydroxyphenyl (DHPD) functionalized polymer (DHPp) of any of paragraphs 1 through 21 and a second polymer, wherein the first and second polymer may be the same or different and wherein the first and second DHPp can be the same or different.

37. A bioadhesive construct comprising:
a support suitable for tissue repair or reconstruction;
a first coating comprising a first multihydroxyphenyl (DHPD) functionalized polymer (DHPp) of any of paragraphs 1 through 21; and
a second coating coated onto the first coating, wherein the second coating comprises a second multihydroxyphenyl (DHPD) functionalized polymer (DHPp) of any of paragraphs 1 through 21, wherein the first and second DHPp can be the same or different.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Materials and Method Development 1.1. Syntheses

Example 1

Synthesis of Surphys-029

Dissolved 10 g of 4-arm PEG-NH$_2$ (10,000 MW; 1 mmol), 600 mg of poly(ethyleneglycol) bis(carboxymethyl)ether (PEG-bCME, Mn ~600, 1 mmol), and 456 mg of 3,4-dihydroxyhydrocinnamic acid (DOHA, 2.5 mmol) with 40 ml chloroform and 20 ml DMF in a round bottom flask equipped with an addition funnel. Added 676 mg of HOBt (5 mmol), 1.9 g of HBTU (5 mmol), and 560 µL of triethylamine (4 mmol) in 30 mL of DMF dropwise to the round bottom flask over a period of 90 minutes. Stirred at room temperature for 2 hours. Added the mixture to 600 mL of diethyl ether. The precipitate was collected via vacuum filtration and dried. The crude product was further purified through dialysis (15,000 MWCO) in deionized H$_2$O (acidified to pH 3.5) for 24 hrs. After lyophilization, 6.3 g of Surphys-029 was obtained. $^1$H NMR (400 MHz, D$_2$O): δ 6.85-6.67 (m, 3H, C$_6$H$_3$(OH)$_2$—), 4.09 (s, 2H, PEG-CH$_2$—O—C(O)—NH—), 3.75-3.28 (m, PEG), 2.8 (t, 2H, C$_6$H$_3$(OH)$_2$—CH$_2$—CH$_2$—C(O)—NH—), 2.51 (t, 2H, C$_6$H$_3$(OH)$_2$—CH$_2$—CH$_2$—C(O)—NH—), UV-vis spectroscopy: 0.21±0.019 µmole DH/mg polymer (3.5±0.32 wt % DH). GPC: Mw=140,000, Mn=43,000, PD=3.3.

Example 2

Synthesis of PCL1.25k-diSA

Added 10 g of polycaprolactone-diol (PCL-diol, MW=1,250, 8 mmol), 8 g of succinic anhydride (SA, 80 mmol), 6.4 mL of pyridine (80 mmol), and 100 mL of chloroform to a round bottom flask (250 mL). Refluxed the solution in a 75-85° C. oil bath with Ar purging for overnight. Allowed the reaction mixture to cool to room temperature and 100 mL of chloroform was added. Washed the mixture successively with 100 mL each of 12.1 mM HCl, saturated NaCl, and deionized water. The organic layer was dried over magnesium sulfate and then the volume of the mixture was reduced by half by rotary evaporator. After pouring the mixture into 800 mL of a 1:1 hexane and diethyl ether, the polymer was allowed to precipitate at 4° C. for overnight. The polymer was collected and dried under vacuum to yield 8.1 g of PCL1.25 k-diSA. $^1$H NMR (400 MHz, DMSO/TMS): δ 12.2 (s, 1H, COOH—), 4.1 (s, 2H, PCL-CO—CH$_2$—CH$_2$—COOH—) 4.0 (s, 12H, O—(CO—CH$_2$—(CH$_2$)$_4$—O)$_6$CO—CH$_2$—CH$_2$—COOH), 3.6 (s, 2H, PCL-CO—CH$_2$—CH$_2$—COOH—) 3.3 (s, 2H, —CH$_2$-PCL$_6$-SA), 2.3 (t, 12H, O—(CO—CH$_2$—(CH$_2$)$_3$—CH$_2$—O)$_6$CO—CH$_2$—CH$_2$—COOH), 1.5 (m, 24H, O—(CO—CH$_2$—CH$_2$—CH$_2$—CH$_2$—CH$_2$—O)$_6$CO—CH$_2$—CH$_2$—COOH), 1.3 (m, 12H, O—(CO—CH$_2$—CH$_2$—CH$_2$—CH$_2$—CH$_2$—O)$_6$CO—CH$_2$—CH$_2$—COOH). Similarly, PCL2k-diSA was synthesized using the procedure with 2,000 MW PCL-diol.

Example 3

Synthesis of PCL2k-diGly

Dissolved 10 g of polycaprolactone-diol (5 mmole, MW 2000) with 2.63 g of Boc-Gly-OH (15 mmole) in 60 mL chloroform and purged with argon for 30 minutes. Added 3.10 g of DCC (15 mmole) and 61.1 mg of DMAP (0.5 mmole) to the reaction mixture and allowed the reaction to proceed overnight with argon purging. Filtered the solution into 400 mL of diethyl ether along with 40 mL of chloroform. The precipitate was collected through filtration and dried under vacuum to yield 4.30 g of PCL2k-di-BocGly. $^1$H NMR (400 MHz, CDCl$_3$/TMS): δ 5.1 (s, 1H, CH$_2$NHCOOC(CH$_3$)$_3$—), 4.2 (t, 2H, CH$_2$NHCOOC(CH$_3$)$_3$—) 4.0 (t, 16H, O—(CO—CH$_2$—(CH$_2$)$_3$CH$_2$—O)$_8$CO—CH$_2$—CH$_2$—COOH), 3.8 (t, 2H, O—CH$_2$CH$_2$—O—CO-PCL), 3.6 (t, 2H, O—CH$_2$CH$_2$—O—CO-PCL), 2.3 (t, 16H, O—CH$_2$CH$_2$—O—CO—CH$_2$(CH$_2$)$_4$—OCO), 1.7 (m, 32H, O—CH$_2$CH$_2$—O—CO—CH$_2$CH$_2$CH$_2$CH$_2$—OCO), 1.5 (s, 9H, CH$_2$NHCOOC(CH$_3$)$_3$), 1.3 (m, 16H, O—CH$_2$CH$_2$—O—CO—CH$_2$CH$_2$CH$_2$CH$_2$—OCO).

Boc protecting group on PCL2k-di-BocGly was removed by reacting the polymer in 14.3 mL of chloroform and 14.3 mL of trifluoroacetic acid for 30 minutes. After precipitated twice in ethyl ether, the polymer was dried under vacuum to yield 3.13 g of PCL2k-diGly. $^1$H NMR (400 MHz, CDCl$_3$/TMS): δ 4.2 (m, 4H, CH$_2$NH$_2$—) 4.0 (t, 16H, O—(CO—CH$_2$—(CH$_2$)$_3$CH$_2$—O)$_8$CO—CH$_2$—CH$_2$—COOH), 3.8 (t, 2H, O—CH$_2$CH$_2$—O—CO-PCL), 3.6 (t, 2H, O—CH$_2$CH$_2$—O—CO-PCL), 2.3 (t, 16H, O—CH$_2$CH$_2$—O—CO—CH$_2$(CH$_2$)$_4$—OCO), 1.7 (m, 32H, O—CH$_2$CH$_2$—O—CO—CH$_2$CH$_2$CH$_2$CH$_2$—OCO), 1.3 (m, 16H, O—CH$_2$CH$_2$—O—CO—CH$_2$CH$_2$CH$_2$CH$_2$—OCO). PCL1.25 k-diGly was synthesized using the similar procedure while using 1,250 MW PCL-diol.

Example 5

Synthesis of Medhesive-054

Dissolved 5 grams of 4-arm PEG-Amine-10k (0.5 mmole) in 20 mL of DMF with 0.625 grams of PCL 1250-diSA (0.5 mmole), and 0.228 g of DOHA (1.25 mmole) in a round bottom flask. To this mixture, HOBt (0.338 grams; 2.5 mmole), HBTU (0.95 grams; 2.5 mmole), and Triethylamine (280 uL; 2.0 mmole) in 20 mL of chloroform and 30 mL of DMF was added dropwise over 60 minutes. After the reaction mixture was stirred for 2 hours, 0.0455 g of DOHA (0.25 mmole) was added and the mixture was further stirred at room temperature for 1 hour. This solution was filtered into diethyl ether and allowed to precipitate at 4° C. for overnight. The precipitate was collected by vacuum filtration and dried under vacuum for 24 hours. The polymer was dissolved in 75 mL of 50 mM HCl and 75 mL of methanol and dialyzed in 4 L of water (acidified to pH 3.5) for 2 using a 15,000 MWCO tube. 3.8 g of Medhesive-054 was obtained after lyophilization. $^1$H NMR (400 MHz, DMSO/TMS): δ 8.7-8.5 (s, 1H, C$_6$H$_3$(OH)$_2$—), 7.9 (d, 2H, C$_6$H$_3$(OH)$_2$—), 6.5 (dd, 1H, C$_6$H$_3$(OH)$_2$—), (dd, 1H, C$_6$H$_3$(OH)$_2$—CH$_2$—CH$_2$—CONH—CH$_2$—CH$_2$—O—), 4.1 (s, 2H, PCL-CO—CH$_2$—CH$_2$—COOH—) 4.0 (s, 12H, O—(CO—CH$_2$—(CH$_2$)$_4$—0)$_6$CO—CH$_2$—CH$_2$—COOH), 3.6 (s, 2H, PCL-CO—CH$_2$—CH$_2$—COOH—) 3.3 (s, 2H, —CH$_2$-PCL$_6$-SA), 2.3 (t, 12H, O—(CO—CH$_2$—(CH$_2$)$_3$—CH$_2$—O)$_6$CO—CH$_2$—CH$_2$—COOH), 1.5 (m, 24H, O—(CO—CH$_2$—CH$_2$—CH$_2$—CH$_2$—O)$_6$CO—CH$_2$—CH$_2$—COOH), 1.3 (m, 12H, O—(CO—CH$_2$—CH$_2$—CH$_2$—CH$_2$—O)$_6$CO—CH$_2$—CH$_2$—COOH). UV-vis spectroscopy: 0.22±0.020 μmole DH/mg polymer (3.6±0.33 wt % DH). GPC: Mw=98,000; Mn=35,000; PD=2.8. (DH=DOHA)

Example 6

Synthesis of Medhesive-061 (PEG20k-(DMu)$_8$)

Dry 50 g of 8-armed PEG-OH (20,000 MW; 20 mmol —OH) via azeotropic evaporation of toluene, followed by drying in a vacuum dessicator. Redissolve PEG in 400 mL toluene, then add 53 mL of phosgene solution (20% phosgene in toluene; 100 mmol phosgene). Stir the mixture at 55° C. for 4 hours with a NaOH solution trap to trap escaped phosgene. Evaporate toluene and dry with vacuum for overnight. Add 350 mL of chloroform and 3.46 g of N-hydroxysuccinimide (30 mmol) to the phosgene-activated PEG, followed by the addition of 4.18 mL (30 mmol) of triethylamine in 30 mL chloroform dropwise. Stir the mixture under Argon for 4 hours. To the reaction mixture, add 7.58 g dopamine-HCl (40 mmol), 11.16 mL triethylamine (80 mmol) and 120 mL DMF, then stir the reaction at room temperature for overnight. Add the reaction mixture to diethyl ether, then collect the precipitate via filtration and dry. The crude product will then be purified further using dialysis (3500 MWCO) in deionized water (acidified to pH 3.5) for 24 hours. PEG20k-(DMu)s [Medhesive-061] $^1$H NMR (400 MHz, DMSO/TMS): δ 8.73-8.63 (d, 2H, C$_6$H$_3$(OH)$_2$—), 7.2 (m, 1H, PEG-C(O)—NH—), 6.62-6.42 (m, 3H, C$_6$H$_3$(OH)$_2$—), 4.04-4.02 (s, 2H, PEG-CH$_2$—O—C(O)—NH—), 3.68 (m, 2H, C$_6$H$_3$(OH)$_2$—CH$_2$—CH$_2$—NH—C(O)—O—), 3.62-3.41 (m, PEG), 3.07 (m, 2H, C$_6$H$_3$(OH)$_2$—CH$_2$—CH$_2$—NH—C(O)—O—). UV-vis spectroscopy: 0.375±0.01 μmole DM/mg polymer (6.84±0.18 wt % DM).

Example 7

Synthesis of Medhesive-096

Combined 10 g of 10K, 4-arm PEG-OH (1 mmole) with toluene (180 mL) in a 500 mL round bottom flask equipped with a condenser, Dean-Stark Apparatus and Argon inlet. While purging with argon, the mixture was stirred in a 140-150° C. oil bath until 90 mL of toluene was removed. The reaction was cooled to room temperature and 10.6 mL (20 mmole) of the 20% phosgene solution in toluene was added. The mixture was further stirred at 50-60° C. for 4 hours while purged with argon while using a 20 Wt % NaOH in a 50/50 water/methanol trap. Toluene was removed via rotary evaporation with a 20 Wt % NaOH solution in 50/50 water/methanol in the collection trap. The polymer was dried under vacuum for overnight. 691 mg (6 mmole) of NHS and 65 mL of chloroform was added to PEG and the mixture was purge with argon for 30 minutes. 840 μl (6 mmole) of triethylamine in 10 mL chloroform was added dropwise and the reaction mixture was stir with argon purging for 4 hours. After which, 427 mg (2.2 mmole) of dopamine hydrochloride in 25 mL of DMF and 307 μl (2.2 mmole) of triethylamine was added and the mixture was stirred for 4 hours. Added 2.4 g (1 mmole) of PCL-Gly along with 280 uL (2 mmole) of triethylamine and the mixture was further stirred for overnight. 133 mg (0.7 mmole) of dopamine hydrochloride was added to cap the reaction along with 98 μl (0.7 mmole) of triethylamine. The mixture was precipitated in ethyl ether and the collected precipitated was dried under vacuum. The crude polymer was dissolved in 150 mL of methanol and 100 mL 50 mM HCl and dialyzed (15000 MWCO dialysis tubing) in 4 L of water at pH 3.5 for 2 days with changing of the water at least 4 times a day. Lyophilization yielded the product. $^1$H NMR (400 MHz, DMSO/TMS): δ 8.7-8.5 (s, 1H, C$_6$H$_3$(OH)$_2$—), 7.6 (t, 1H, -PCL-O—CH$_2$—CH$_2$—NHCOO—CH$_2$—CH$_2$—O—)), 7.2

(t, 1H, —O—CH$_2$—CH$_2$—NHCOO—CH$_2$—CH$_2$—C$_6$H$_3$(OH)$_2$—), 6.7 (d, 1H, C$_6$H$_3$(OH)$_2$—), 6.5 (s, 1H, C$_6$H$_3$(OH)$_2$—), 6.4 (s, 1H, C$_6$H$_3$(OH)$_2$—), 4.0 (t, 16H, O—(CO—CH$_2$—(CH$_2$)$_3$CH$_2$—O)$_8$CO—CH$_2$—CH$_2$—COOH), 3.5 (m, PEG, —O—CH$_2$—CH$_2$—O—), 2.3 (t, 16H, —O—CH$_2$CH$_2$—O—CO—CH$_2$(CH$_2$)$_4$—OCO—), 1.7 (m, 32H, —O—CH$_2$CH$_2$—O—CO—CH$_2$CH$_2$CH$_2$CH$_2$—OCO—), 1.3 (m, 16H, —O—CH$_2$CH$_2$—O—CO—CH$_2$CH$_2$CH$_2$CH$_2$CH$_2$—OCO—); DH Wt %=2.34%; PCL Wt %=20.7%. UV-vis spectroscopy: 0.211±0.069 μmole DH/mg polymer (2.92±0.34 wt % DH). GPC: Mw=65,570; Mn=14,850; PD=4.4.

Example 8

Synthesis of Medhesive-104

Dissolve 1.02 g of PCL2k-diSA (0.46 mmole) with 5 g of, 10k, 4-arm-PEG-NH$_2$ (0.5 mmol) and 0.228 g of DOHA (1.25 mmol) in a 250 mL round bottom flask containing 20 mL of DMF. Dissolve 0.338 g (2.5) of HOBt, 0.95 g (2.5 mmol) HBTU, and 280 uL (2 mmole) of triethylamine in 35 mL of DMF followed by the addition of 20 mL of chloroform. The HOBt/HBTU/TEA solution was added dropwise over a period of 40 minutes. This was then allowed to stir for an additional 2 hours. A second addition of 0.045 g (0.25 mmol) of DOHA was added to the solution and allowed to react for an addition 30 minutes. Filter solution into diethyl ether. Place at 4 C for 24 hours and filter the precipitate. Dry in dessicator for an additional 24 hours. Dissolve polymer in 75 mL of 100 mM HCl and 100 mL of MeOH. Filter the solution using coarse filter paper and dialyze (15000 MWCO dialysis tubing) in 4 L of water at pH 3.5 for 2 days with changing of the water at least 4 times a day. Lyophilization yielded the product.

$^1$H NMR (400 MHz, DMSO/TMS): δ 8.7-8.5 (s, 1H, C$_6$H$_3$(OH)$_2$—), 7.9 (d, 2H, C$_6$H$_3$(OH)$_2$—), 6.5 (dd, 1H, C$_6$H$_3$(OH)$_2$—), (dd, 1H, C$_6$H$_3$(OH)$_2$—CH$_2$—CH$_2$—CONH—CH$_2$—CH$_2$—O—), 4.1 (s, 2H, PCL-CO—CH$_2$—CH$_2$—COOH—) 4.0 (s, 16H, O—(CO—CH$_2$—(CH$_2$)$_4$—O)$_6$CO—CH$_2$—CH$_2$—COOH), 3.6 (s, 2H, PCL-CO—CH$_2$—CH$_2$—COOH—) 3.3 (s, 2H, —CH$_2$-PCL$_6$-SA), 2.3 (t, 16H, O—(CO—CH$_2$—(CH$_2$)$_3$—CH$_2$—O)$_6$CO—CH$_2$—CH$_2$—COOH), 1.5 (m, 32H, O—(CO—CH$_2$—CH$_2$—CH$_2$—CH$_2$—CH$_2$—O)$_6$CO—CH$_2$—CH$_2$—COOH), 1.3 (m, 16H, O—(CO—CH$_2$—CH$_2$—CH$_2$—CH$_2$—CH$_2$—O)$_6$CH$_2$—CH$_2$—COOH); DH Wt %=1.17%; PCL Wt %=27.5%. UV-vis spectroscopy: 0.091±0.009 μmole DH/mg polymer (1.49±0.15 wt % DH).

Example 9

Synthesis of Medhesive-105

Combine 40 g of 10K, 4-arm PEG-OH (4 mmole) with toluene (240 mL) in a 500 mL round bottom flask equipped with a condenser, Dean-Stark Apparatus and Argon inlet. While purging with argon, heat reaction to 140-150° C. and stir till half the volume has been removed. Cool the reaction to room temperature. Add 42.4 mL (80 mmole) of the phosgene solution using a syringe. Stir mixture at 50-60 C for 4 hours while purging with argon using a 20 Wt % NaOH in a 50/50 water/methanol trap. Remove toluene via rotary evaporation with a 20 Wt % NaOH solution in 50/50 water/methanol in the collection trap. Dry under vacuum overnight.

Add 2.77 g (24 mmole) of NHS to PEG followed by addition of 260 mL chloroform. Purge with argon for 30 minutes and add 3.36 mL (24 mmole) of triethylamine in 40 mL chloroform dropwise. Stir with argon purging for 4 hours.

To PEG-NHS solution add 1.71 g (8.8 mmole) of dopamine hydrochloride in 75 mL DMF along with 1.23 m L (8.8 mmole) of triethylamine. Let react for 4 hours.

Add 6.0 g (4.2 mmole) of PCL1250-(Gly)$_2$ along with 1.12 mL (8 mmole) of triethylamine. Let react for 16 hours. Add an additional 532 mg (2.8 mmole) dissolved in 25 mL DMF along with 392 μL triethylamine. Stir for 3.5 hours. Add reaction mixture to 1.6 L diethyl ether and place into 4° C. for overnight. The solution was suction filtered and dried under vacuum for several days. This was then dissolved in 600 mL of methanol and 400 mL 50 mM HCl. This was then filtered using coarse filter paper and dialyzed (15000 MWCo dialysis tubing) in 10.5 L of water at pH 3.5 for 2 days with changing of the water at least 4 times a day. The solution was then freeze dried and placed under a vacuum for 4-24 hours. After drying, $^1$H NMR, GPC and UV-VIS were used to determine purity and coupling efficiency of the catechol.

P(CL1.25EG10kb-g-DH2) [Medhesive-105] L/N 003281. $^1$H NMR (400 MHz, DMSO/TMS): DH:PEG:PCL=2:1.23:1.09. UV-vis spectroscopy: 0.237±0.008 μmole DH/mg polymer (3.92±0.14 wt % DH). GPC: Mw=320,000 Da; PD=6.892

Example 10

Synthesis of HO-PCL-PEG(600)-PCL-OH 26.3 g of PEG-diol (43.8 mmol, MW 600) and 200 mL of toluene was added and the mixture was heated in 155-165° C. oil bath with Ar purging until 50 mL of toluene was collected. 100 g of ε-caprolactone (876 mmol) was added and heated until 20 mL of toluene was evaporated. Added 1.135 μL (3.50 mmol) of tin(II) 2-ethylhexanoate was added. The mixture was stirred for another 20 hrs in a 155-165° C. oil bath with Ar purging. The clued polymer was purified by ether precipitation twice to yield 54.2 g of polymer. Based on $^1$H NMR, each PCL block consists of 21.2 caprolactone units with the overall number average MW of the polymer calculated to be 5,400 Da.

Synthesis of SA-PCL-PEG(600)-PCL-SA (Medhesive-112 Starting Material)

Add 25 g of HO-PCL-PEG(600)-PCL-OH (MW~5400; 4.63 mmole) with 4.63 g of succinic anhydride (46.3 mmole) and 3.74 mL of pyridine (46.3 mmole) to chloroform (250 mL) in a round bottom flask (500 mL). Reflux the solution at 75-85° C. in an oil bath with argon purging for 24 hours. Allow the reaction to cool to room temperature and add another 250 mL of chloroform to the solution. Wash the mixture with 250 mL of 12.1 mM HCl, followed by 250 mL of saturated NaCl, followed by 250 mL of DI water. Dry the solution with magnesium sulfate for 24 hours. Filter the magnesium sulfate with coarse filter paper and reduce the volume of the filtrate by half using the roto evaporator. Filter the mixture into 4 L of a 1:1 mixture of hexane and diethyl ether and let this sit at 4° C. for 24 hours. Suction filter the solution and allow it to dry under vacuum for 24 hours. Weigh out the dried sample. Dissolve in 250 mL of chloroform and precipitate into 2.4 L of a 1:1 mixture of hexane and diethyl ether and let this sit at 4° C. for 24 hours. Suction filter the solution and allow it to dry under vacuum for 24 hours. Weigh out the dried sample. This has 69% coupling efficiency of SA so repeat synthesis using the following method.

Take 17.5 g of product from previous reaction, along with 4.63 g of succinic anhydride (46.3 mmole) and dissolve in 500 mL of chloroform. Add 3.74 mL of pyridine (46.3 mmol)

and reflux the solution at 75-85° C. in an oil bath with argon purging for 18 hours. Allow the reaction to cool to room temperature. Wash the mixture with 250 mL of 12.1 mM HCl, followed by 250 mL of saturated NaCl, followed by 250 mL of DI water. Dry the solution with magnesium sulfate for at least 24 hours. Filter the magnesium sulfate with coarse filter paper and reduce the volume of the filtrate by half using the roto evaporator. Filter the mixture into 3.6 L of a 1:1 mixture of hexane and diethyl ether and let this sit at 4° C. for 24 hours. Suction filter the solution and allow it to dry under vacuum for 24 hours. Weigh out the dried sample.

HOOC-PCL-PEG(600)-PCL-COOH L/N 004973. $^1$H NMR (400 MHz, CDCl$_3$): δ 4.1 (s, 2H, PCL-CO—CH$_2$—CH$_2$—COOH—) 4.0 (s, 42H, O—(CO—CH$_2$—(CH$_2$)$_4$—O)$_{21}$CO—CH$_2$—CH$_2$—COOH), 3.6 (s, 2H, PCL-CO—CH$_2$—CH$_2$—COOH—) 3.3 (s, 2H, —CH$_2$-PCL$_{21}$-SA), 2.3 (t, 42H, O—(CO—CH$_2$—(CH$_2$)$_3$—CH$_2$—O)$_{21}$CO—CH$_2$—CH$_2$—COOH), 1.5 (m, 24H, O—(CO—CH$_2$—CH$_2$—CH$_2$—CH$_2$—CH$_2$—O)$_{21}$CO—CH$_2$—CH$_2$—COOH), 1.3 (m, 12H, O—(CO—CH$_2$—CH$_2$—CH$_2$—CH$_2$—CH$_2$—O)$_{21}$CO—CH$_2$—CH$_2$—COOH)

Synthesis of Medhesive-112

Dissolve 21.43 grams of 4-arm PEG-Amine-10k (2.14 mmole) in 100 mL of DMF and 45 mL of chloroform with 12 grams of HOOC-PCL-PEG(600)-PCL-COOH (2.14 mmole), and 0.977 g of DOHA (5.36 mmole) in a round bottom flask. Dissolve HOBt (1.45 grams; 10.7 mmole), HBTU (4.06 grams; 10.7 mmole), and triethylamine (2.075 mL; 14.97 mmole) in 85 mL of chloroform and 130 mL of DMF. Add the HOBt/HBTU/Triethylamine solution dropwise to the PEG/PCL/DOHA reaction over a period of 30-60 minutes. Stir the reaction for 24 hours. Add 0.594 grams of DOHA (3.26 mmole) to the reaction and let it stir for 4 hour. Filter this solution into 3.6 L of diethyl ether and place at 4° C. for 16-24 hours. Suction filter the precipitate and dry under vacuum for 16-24 hours. Dissolve the polymer in 400 mL of methanol and 120 mL of DMF. This was then dialyzed using 15000 MWCO dialysis tubing against 10 L of water acidified to pH 3.5 for 3 days. The acidified water was changed at least 4 times daily. The solution was then freeze dried and placed under a vacuum for 4-24 hours. After drying, $^1$H NMR and UV-VIS were used to determine purity and coupling efficiency of the catechol.

P(CL5.4(EG600)EG10kb-g-DH2) [Medhesive-112] L/N's 005504. $^1$H NMR (400 MHz, DMSO/TMS): δ 8.7-8.5 (s, 1H, C$_6$H$_3$(OH)$_2$—), 7.9 (s, 1H, C$_6$H$_3$(OH)$_2$—CH$_2$—CH$_2$—CONH—CH$_2$—CH$_2$—O—), 7.8 (s, 1H, -PCL-COO—CH$_2$—CH$_2$—CONH—CH$_2$—CH$_2$—O—), 6.6 (d, 1H, C$_6$H$_3$(OH)$_2$—), 6.5 (s, 1H, C$_6$H$_3$(OH)$_2$—), 6.4 (d, 1H, C$_6$H$_3$(OH)$_2$—CH$_2$—CH$_2$—CONH—CH$_2$—CH$_2$—O—), 4.1 (s, 2H, PCL-CO—CH$_2$—CH$_2$—CONH—CH$_2$—CH$_2$—O-PEG) 4.0 (s, 84H, O—(CO—CH$_2$—(CH$_2$)$_4$—O)$_{21}$CO—CH$_2$—CH$_2$—CONH), 3.6 (m, 278H, PEG), 1.5 (m, 168H, O—(CO—CH$_2$—CH$_2$—CH$_2$—CH$_2$—CH$_2$—O)$_{21}$CO—CH$_2$—CH$_2$—CONH), 1.3 (m, 84H, O—(CO—CH$_2$—CH$_2$—CH$_2$—CH$_2$—O)$_{21}$CO—CH$_2$—CH$_2$—CONH). $^1$H NMR: Wt % DOHA=1.81%; Wt % PCL=24.7%. UV-vis spectroscopy: 0.124±0.002 μmole DH/mg polymer (2.05±0.03 wt % DH).

Example 11

Synthesis of HO-PLA-PEG(600)-PLA-OH 14.9 g of PEG-diol (24.8 mmol, MW 600) was azeotropically dried with rotary evaporation using 50 mL of toluene twice and dried with vacuum pump for overnight. 50 g of L-lactide (347 mmol) and 100 mL of toluene was added and the mixture was heated in 155-165° C. oil bath with Ar purging until 50 mL of toluene was collected. The mixture was allow to cool for 10 min and then 643 μL (1.98 mmol) of tin(II) 2-ethylhexanoate was added. The mixture was stirred for another 24 hrs in a 155-165° C. oil bath with Ar purging. The clued polymer was purified by ether precipitation twice to yield 35.7 g of polymer. Based on $^1$H NMR, each PLA block consists of 25.0 lactide unit with the overall number average MW of the polymer calculated to be 4,200 Da.

Synthesis of SA-PLA-PEG(600)-PLA-SA

Add 25 g of HO-PLA-PEG(600)-PLA-OH (MW 4,200; 6 mmole) with 11.91 g of succinic anhydride (119 mmole) and 9.63 mL of pyridine (119 mmole) to chloroform (250 mL) in a round bottom flask (500 mL). Reflux the solution at 75-85° C. in an oil bath with argon purging for 24 hours. Allow the reaction to cool to room temperature and add another 250 mL of chloroform to the solution. Wash the mixture with 250 mL of 12.1 mM HCl, followed by 250 mL of saturated NaCl, followed by 250 mL of DI water. Dry the solution with magnesium sulfate for 24 hours. Filter the magnesium sulfate with coarse filter paper and reduce the volume of the filtrate by half using the roto evaporator. Filter the mixture into 2.4 L of a 1:1 mixture of hexane and diethyl ether and let this sit at 4° C. for 24 hours. Suction filter the solution and allow it to dry under vacuum for 24 hours. Weigh out the dried sample.

SA-PLA-PEG(600)-PLA-SA L/N 005525. $^1$H NMR (400 MHz, CDCl$_3$): δ 5.2 (q, 25H, (OCHCH$_3$CO)$_{25}$—), 4.3 (m, 2H, PLA-COO—CH$_2$—CH$_2$—O-PEG-) 3.7-3.6 (m, 56H, PLA-(O—CH$_2$—CH$_2$)$_{14}$-PLA), 2.7-2.6 (m, 4H, PLA-CO—CH$_2$—CH$_2$—COOH—) 1.6-1.5 (d, 75H, (OCHCH$_3$CO)$_{25}$—).

Synthesis of Medhesive-116

Dissolve 45 grams of 4-arm PEG-Amine-10k (4.5 mmole) in 180 mL of DMF with 19.8 grams of SA-PLA-PEG(600)-PLA-SA (4.5 mmole), and 2.05 g of DOHA (11.3 mmole) in a round bottom flask. Dissolve HOBt (3.04 grams; 22.5 mmole), HBTU (8.53 grams; 22.5 mmole), and Triethylamine (4.356 mL; 31.4 mmole) in 180 mL of chloroform and 270 mL of DMF. Add the HOBt/HBTU/Triethylamine solution dropwise to the PEG/PCL/DOHA reaction over a period of 30-60 minutes. Stir the reaction for 24 hours. Add 1.25 g of DOHA (6.8 mmole) to the reaction and let it stir for 4 hour. Filter this solution into 3.2 L of diethyl ether and place at 4° C. for 24 hours. Suction filter the precipitate and dry under vacuum for 16-24 hours. Dissolve the polymer in 350 mL of DMF. Once completely dissolved, slowly add 450 mL of methanol. This was then placed in 15000 MWCO dialysis tubing and dialyzed in 20 L of water at pH 3.5 for 3 days with changing of the water at least 4 times a day. The solution was then freeze dried and placed under a vacuum for 4-24 hours. After drying, $^1$H NMR and UV-VIS were used to determine purity and coupling efficiency of the catechol.

P(LA4.2(EG600)EG10kb-g-DH2) [Medhesive-116] L/N's 003104. $^1$H NMR (400 MHz, DMSO/TMS): δ 8.7-8.5 (s, 1H, C$_6$H$_3$(OH)$_2$—), 7.9 (s, 1H, C$_6$H$_3$(OH)$_2$—CH$_2$—CH$_2$—CONH—CH$_2$—CH$_2$—O—), 7.8 (s, 1H, -PLA-COO—CH$_2$—CH$_2$—CONH—CH$_2$—CH$_2$—O—), 6.6 (d, 1H, C$_6$H$_3$(OH)$_2$—), 6.5 (s, 1H, C$_6$H$_3$(OH)$_2$—), 6.4 (d, 1H, C$_6$H$_3$(OH)$_2$—CH$_2$—CH$_2$—CONH—CH$_2$—CH$_2$—O—), 5.2 (q, 50H, (PEG-(OCHCH$_3$CO)$_{25}$)$_2$—), 4.2 (s, 2H, NH—CH$_2$—CH$_2$—O-PEG-), 3.7-3.1 (m, 278H, PEG), 2.6-2.2 (m, 4H, -PLA-COO—CH$_2$—CH$_2$—CONH—CH$_2$—CH$_2$—O—), 2.6-2.2 (m, 4H, C$_6$H$_3$(OH)$_2$—CH$_2$—CH$_2$—CONH—CH$_2$—CH$_2$—O—), 1.6-1.5 (d, 150H, (PEG-(OCHCH$_3$CO)$_{25}$)$_2$—). $^1$H NMR: 2.77 Wt % DOHA; 21.02

Wt % PLA. UV-vis spectroscopy: 0.147±0.004 μmole DH/mg polymer (2.43±0.07 wt % DH).

Molecular Weight Determination Using Gel Permeation Chromatography (GPC)

Molecular weight of polymers described herein were determined by gel permeation chromatography in concert with triple-angle laser light scattering on a Optilab® rEX (Wyatt Technology) refractive index detector and a miniDAWN™ TREOS (Wyatt Technology) triple-angle light scattering detector using Shodex-OH Pak columns (SB-804 HQ and SB-802.5 HQ) in a mobile phase of 50:50 mixture of methanol and phosphate buffered saline. For the molecular weight calculation, the experimentally determined reflective index (dn/dc) value of the polymer was used.

2.1. Materials Used.

Medhesive-054 and Medhesive-096 were prepared as described above and their corresponding structure and composition can be seen in FIG. 1. ACS certified methanol and chloroform, along with 100×15 mm Fisherbrand petri dishes and concentrated phosphate buffered saline powder (diluted to 1× with 10 L of nanopure water) were obtained from Fisher Scientific. Bovine pericardium was obtained from Nirod Corporation, while the sodium periodate, 99.8+%, A.C.S. reagent was acquired from Sigma-Aldrich. A large number of 91×91 cm cover chip trays were purchased from Entegris, Inc. Poly (vinyl alcohol), 99+% hydrolyzed (89,000-98,000 MW) and poly(caprolactone)-diol (1250 MW) was purchased from Sigma-Aldrich, while poly(caprolactone)-triol (900 MW) was purchased from Acros.

2.2. Method for Coating Bioadhesive Polymer onto Bovine Pericardium Backing for Burst Strength Testing.

The bovine pericardium was cut so as to fit in an 88 mm diameter petri dish. Once placed inside the petri dish the bovine pericardium was flattened so that a smooth surface to coat was obtained and was placed in the fridge for 1 hour.

To the bovine pericardium was added ~371 mg of Medhesive-054 or Medhesive-096, in 5 mL of methanol or 5 mL of chloroform, respectively, to obtain a coating thickness of ~61 g/m$^2$. The variations in solvents was due to different solubility properties. Both bioadhesive polymers coated on bovine pericardium were then placed at 37° C. for 1 hour to remove most of the methanol or chloroform. This was then placed in the dessicator for at least 4 hours to ensure all methanol or chloroform was removed.

2.3. Method for Preparing Bovine Pericardium Defects for Burst Strength Testing.

Bovine pericardium was cut into squares ~40 cm in length and width and to these a 3 mm defect was punched in the center.

2.4. Preparation of Collagen Defects for Burst Strength Testing.

A PTFE sheet was coated with a thin layer of petroleum jelly, to which, the bovine pericardium defect was placed on and smoothed out. Surgical gauze was then placed over the bovine pericardium defects so that the defects were allowed to stay hydrated but did not contain any excess moisture that could interfere with the adhesion of the bioadhesive-coated bovine pericardium backing 2.5 Method of Preparing Bioadhesive-Coated Bovine Pericardium Sheets for Burst Strength Tests.

Once the bioadhesive-coated bovine pericardium backing was dry it was cut into 10 mm circles. To the bovine pericardium defect was placed 31.7 uL of a 20 mg/mL solution of NaIO$_4$. The 10 mm circles of bioadhesive-coated bovine pericardium backing was then placed over the bovine pericardium defects. A glass plate was placed over the top of two of these substrates with the subsequent addition of a 100 gram weight to the top of the glass plate. After 2 hours the weight and glass plate are removed and the corresponding substrates were placed in PBS 1× buffer for 1 hour at 37° C. Following this burst strength tests were performed with the results being reported in Section 3.1.

2.6. Method for Coating Bioadhesive Polymer onto Bovine Pericardium Backing for Lap Shear Testing.

In general, the coating of the bovine pericardium backing with the bioadhesive polymer was performed in the following manner. The bovine pericardium was cut so as to fit in a 91×91 mm cover chip tray. Once placed inside the petri dish the bovine pericardium was flattened so that a smooth surface to coat was obtained.

To the bovine pericardium was added ~505 mg of Medhesive-054 or Medhesive-096, in 5 mL of methanol or 5 mL of chloroform, respectively, to obtain a coating thickness of ~61 g/m$^2$. The variations in solvents was due to different solubility properties. Both bioadhesive polymers coated on bovine pericardium were then placed at 37° C. for 1 hour to remove most of the methanol or chloroform. This was then placed in the dessicator for at least 4 hours to ensure all methanol or chloroform was removed.

In earlier cases the coating was cut in a 4×6 inch sheet of bovine pericardium and placed so that the middle portion was in a 1×4 inch groove. To this, 154 mg of the bioadhesive polymer in 2 mL of methanol and chloroform was poured on the surface and evaporated as described earlier, or they were coated as in Section 2.2. In addition a film applicator may be used in the future to coat these backings 2.7. Method for Preparing Bovine Pericardium Substrates For Lap Shear Testing.

Bovine pericardium was cut into 1"×3" rectangles.

2.8. Method of Preparing Bioadhesive-Coated Bovine Pericardium Sheets for Lap Shear Tests.

Once the bioadhesive-coated bovine pericardium backing was dry it was cut into 1×3 inch circles. To the bovine pericardium substrate was placed 40 uL of a 20 mg/mL solution of NaIO$_4$. The 1×3 inch bioadhesive-coated bovine pericardium backing was then placed over the 1×3 inch bovine pericardium substrates such that there was a 1 cm by 1 inch overlap for a total overlapping area of 0.000254 m$^2$. A glass plate was placed over the top of these substrates with the subsequent addition of a 100 gram weight to the top of the glass plate. After 2 hour the weight and glass plate were removed and the corresponding substrates were placed in PBS 1× buffer for 1 hour at 37° C. Following this burst strength tests were performed with the results being reported in Section 3.2.

2.9. Method of Preparing Blended Bioadhesive/PCL-Coated Bovine Pericardium Sheets for Lap Shear Tests.

The samples were prepared in the same fashion as described in Section 2.6 through 2.8. The major difference being that chloroform was used as a solvent and PCL-diol (MW=530) or PCL-triol (MW=900) was used along with Medhesive-054 at given weight percents. In all cases Medhesive-054 was placed at a coating weight of 61 g/m$^2$.

3.0. Method of Preparing Blended Bilayer Bioadhesive/PCL-Coated Bovine Pericardium Sheets for Lap Shear Tests.

The samples were prepared as in Section 2.9, however, after the evaporation of chloroform a second addition of 50.5 mg of Medhesive-054 in 5 mL of water was added to the bovine pericardium. The water was evaporated off and the bilayer bioadhesive/PCL-coated bovine pericardium sheet was placed in the dessicator overnight.

3.1. Method of Preparing Blended Trilayer Bioadhesive/PCL-Coated Bovine Pericardium Sheets for Lap Shear Tests.

To the bovine pericardium was added ~50.5 mg of Medhesive-054 in 5 mL of water to obtain a coating thickness of ~6.1 g/m$^2$. After this, the solvent was allowed to partially evaporate at 37° C., an addition of 505 mg and 252.5 mg of M-054 and PCL-triol, respectively, in chloroform was then added and the solvent was again allowed to evaporate off at 37° C. Following this, a third and final addition of 50.5 mg of Medhesive-054 in 5 mL of water was added and the solvent was once again allowed to evaporate off at 37° C. Once the solvent had been evaporated off the trilayer bioadhesive/PCL-coated bovine pericardium was placed in the dessicator overnight.

3.2. Method of Preparing Blended Bioadhesive/PVA-Coated Bovine Pericardium Sheets for Lap Shear Tests.

The PVA is insoluble in methanol and can only be dissolved through heating in water. Once dissolved in water it can remain in solution at room temperature. In contrast, Medhesive-054 is relatively insoluble in water and soluble in methanol. If a solution of 2.5 mL of Medhesive-054 in methanol is placed in a solution of 2.5 mL of PVA in water the PVA precipitates out of solution. To combat this problem, PVA was dissolved in 1.25 mL of water through heating. After this, methanol was added in 0.25 mL increments with heating between each increment until the final volume was 2.5 mL. Medhesive-054 was subsequently dissolved in 1.25 mL of methanol. Once dissolved, water was added in 0.25 mL increments with sonication between each addition until the final concentration equaled 2.5 mL. If the two solutions are added together, PVA and Medhesive-054 begin to precipitate out. To overcome this problem the PVA solution is added in 0.25 mL increments to the Medhesive-054 solution along with 0.25 mL of water with sonication after each addition. After these additions the final volume is 7.5 mL. This volume does not fully cover the surface area so water and methanol can be added in 0.25 mL increments to the solution such that the final volume is 10 mL with 6.25 mL being water and 3.75 mL being methanol. The solvent was then evaporated off at 37° C. and placed in the dessicator overnight.

3.3. Method of Preparing Blended Trilayer Bioadhesive/PVA-Coated Bovine Pericardium Sheets for Lap Shear Tests.

To the bovine pericardium was added ~50.5 mg of Medhesive-054 in 5 mL of methanol to obtain a coating thickness of ~6.1 g/m$^2$. This was then placed at 37° C. for 1 hour to remove most of the methanol. After this a second addition as described in section 3.2 was added. Once the solvent had been evaporated off a third and final addition of 50.5 mg of Medhesive-054 was added in 5 mL of water. The solvent was then evaporated off at 37° C. and placed in the dessicator overnight.

3.4. Method of Statistical Analysis.

Statistical analysis was performed with SPSS using One-way Anova by means of Post Hoc Testing using Tukey. All statistical analysis was performed at the 95% confidence interval with the positive control being Dermabond and the negative control being Tisseal in the case for lap shear testing. With burst strength testing the positive control was Dermabond and the negative control is Medhesive-061. For lap shear testing with blended and multi-layered formulations, Dermabond and the single-layered formulation of Medhesive-054 are used as the positive and negative control, respectively.

Results and Discussions 4.1. Burst Strength Testing.

Figure 2:
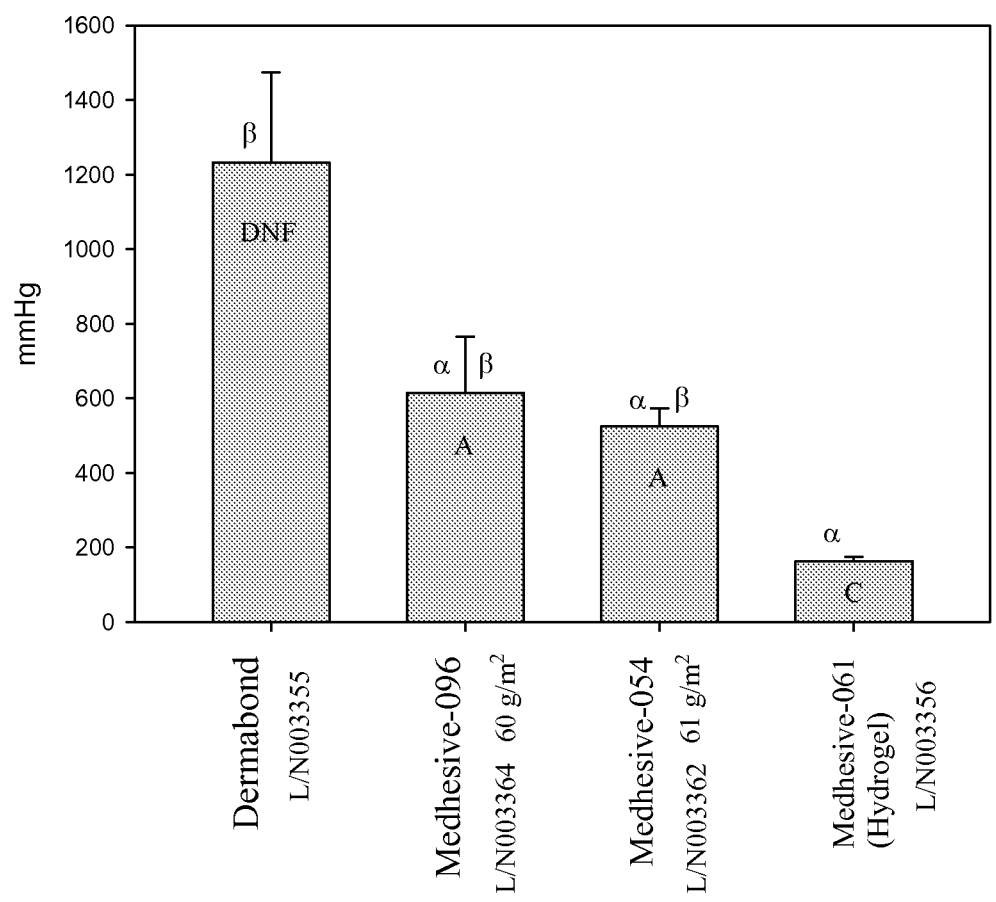
FIG. 2 depicts peak stress required to separate two pieces of adhered collagen sheets in burst strength test. Mode of failure: DNF=Did not fail; A=Adhesive failure; C=Cohesive failure. $\alpha$=statistically different from Dermabond; $\beta$=statistically different from Medhesive-061. ($p$=0.05).

Results for burst strength testing of thin filmed bioadhesive-coated bovine pericardium backings showed performances 4 times better than normal catechol cross linked hydrogels (Medhesive-061) as shown in FIG. 2. However, when compared to Dermabond, there are significant differences in that Medhesive-054 and Medhesive-096 failed adhesively, while Dermabond did not break due to fear of breaking the burst strength tester, which was only accurate up to 800 mmHg.

4.2. Lap Shear Testing.

Figure 3:
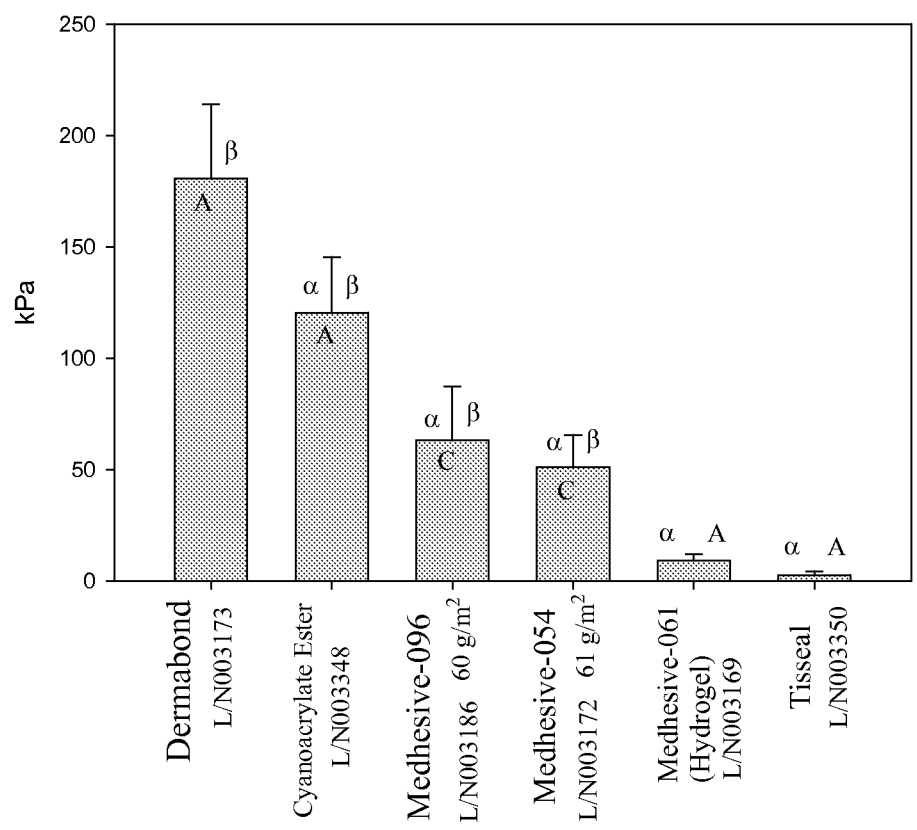
FIG. 3 provides a graphical representation of peak stress required to separate two pieces of adhered collagen sheets in lap shear mode. Mode of failure: A=Adhesive failure; C=Cohesive failure. $\alpha$=statistically different from Dermabond; $\beta$=statistically different from Medhesive-061. ($p$=0.05).

As shown in FIG. 3, lap shear adhesion strength of our thin-film bioadhesive performed 6-8 times better than adhesive hydrogels (Medhesive-061; failure at 8.9 kPa). Both Medhesive-054 and Medhesive-096 failed cohesively with the lap shear strength of 51 kPa and 63 kPa, respectively. Cyanoacrylate ester failed adhesively at 120 kPa while Dermabond performed the best, failing adhesively at 180 kPa. Tisseal performed the worst with a value of 2.6 kPa.

4.3. Lap Shear Testing on Blending Medhesive-054 with PCL.

Figure 4:
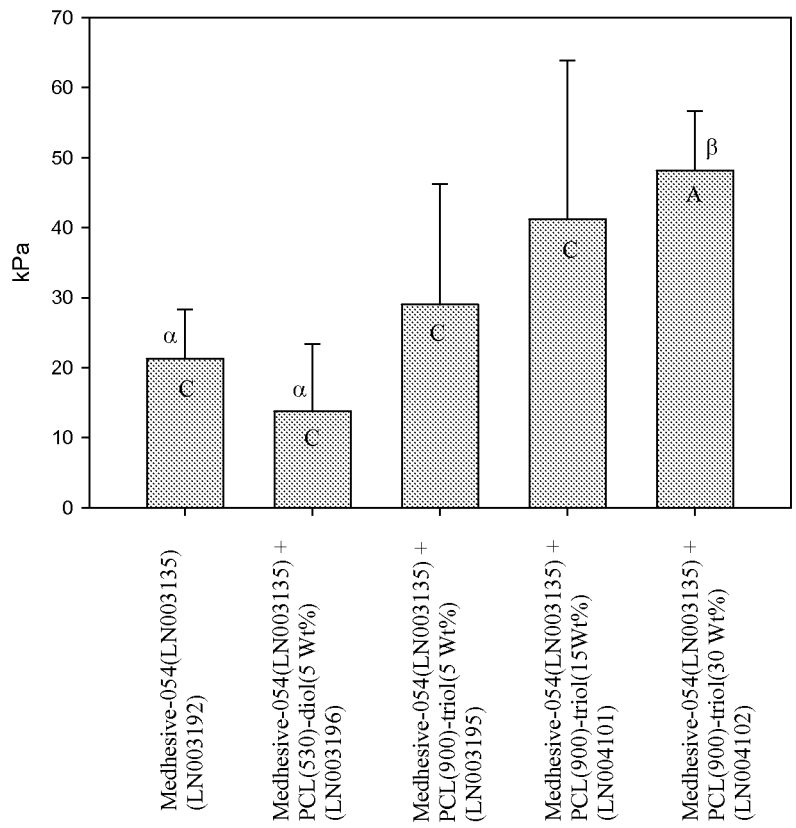
FIG. 4 shows peak stress required to separate two pieces of adhered collagen sheets in lap shear mode. Mode of failure: A=Adhesive failure; C=Cohesive failure. $\beta$=statistically different from Medhesive-054 (LN003135). ($p$=0.05).

A blend of Medhesive-054 and either PCL-diol (MW=530) or PCL-triol (900 MW) were coated onto the pericardium and the maximum lap shear strength was determined. As shown in FIG. 4, PCL-diol did not increase the lap shear strength. However, lap shear strength increased with increasing PCL-triol content. At the highest concentration of PCL-triol tested (30 wt %), the formulation failed at the adhesive substrate interface as oppose to cohesive failure. The results here indicated that the cohesive properties of the adhesive film and the overall strength of the adhesive joint can be increased by incorporation of PCL-triol.

4.4. Lap Shear Testing Comparison of Blending Bilayer Formulations Using PCL.

Figure 5:
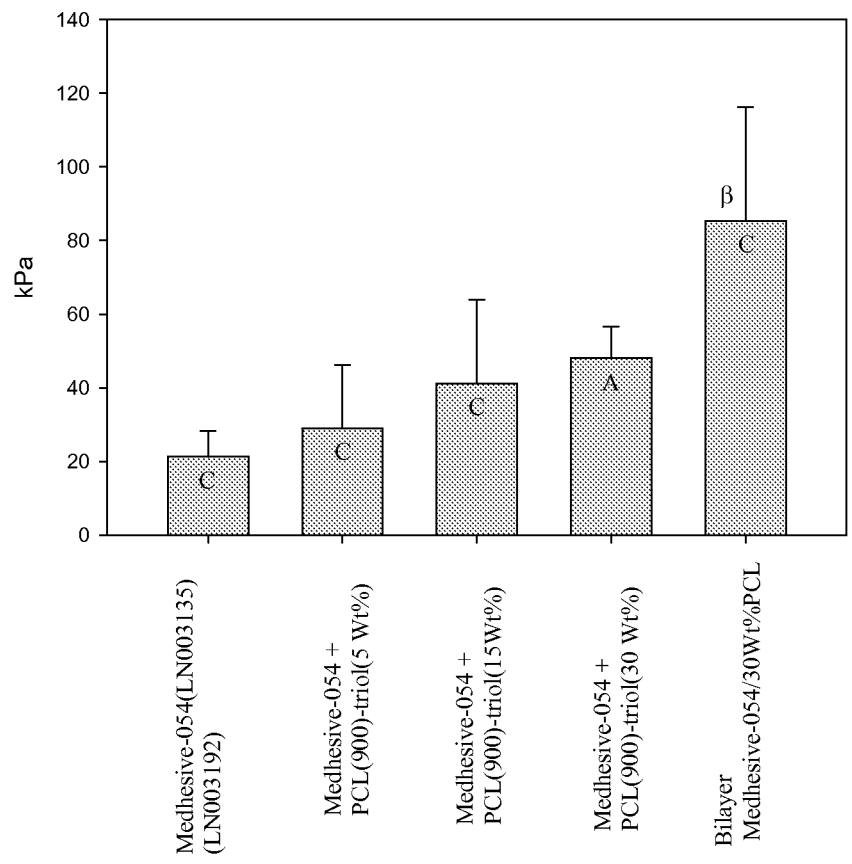
FIG. 5 provides peak stress required to separate two pieces of adhered collagen sheets in lap shear mode. Mode of failure: A=Adhesive failure; C=Cohesive failure. $\beta$=statistically different from Medhesive-054. ($p$=0.05).

Upon addition of the second coating a very dramatic result was observed for the PCL blended formulations. FIG. 5 demonstrates that adding a second coating quadruples the peak stress value as compared to Medhesive-054 by itself. In addition, the primary mode of failure returned to a cohesive failure. Furthermore the statistical difference between the blended formulations from previous data were not statistically different than the control (Medhesive-054), however, the bilayer coating was.

Figure 6:
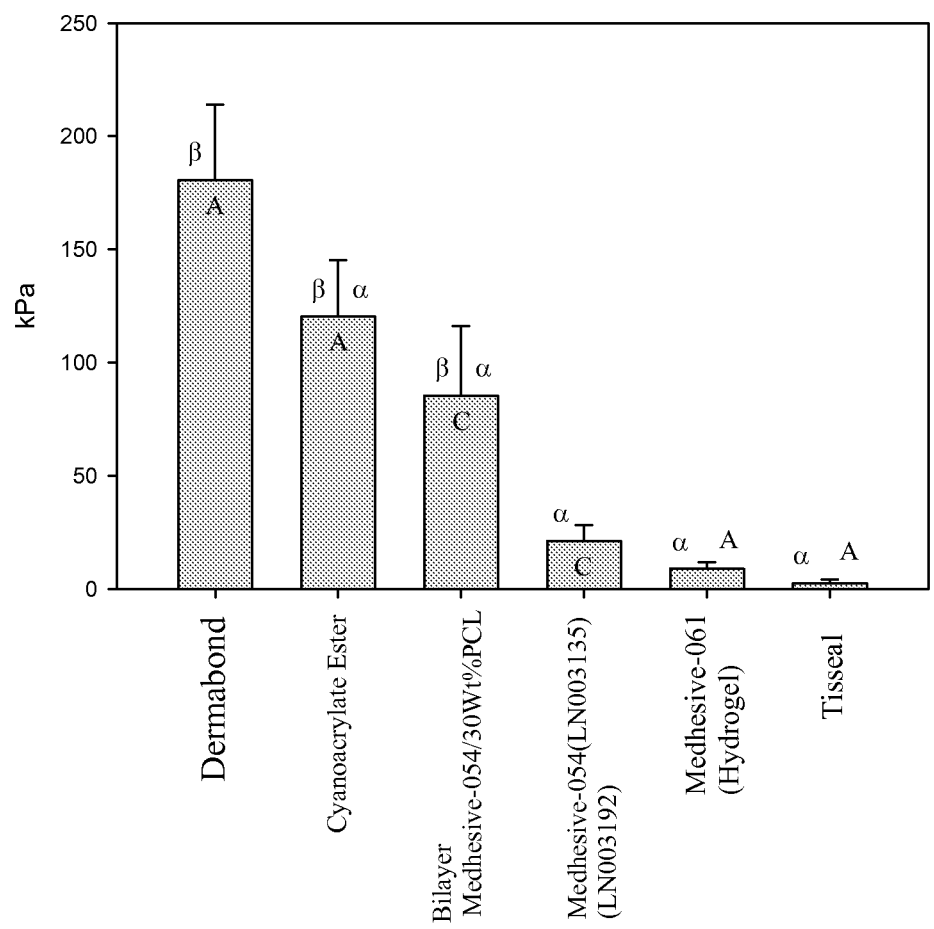
FIG. 6 shows peak stress required to separate two pieces of adhered collagen sheets in lap shear mode. Mode of failure: A=Adhesive failure; C=Cohesive failure. $\alpha$=statistically different from Dermabond; $\beta$=statistically different from Medhesive-061. ($p$=0.05).

In FIG. 6, the data from FIG. 5 is compared to Medhesive-061 as the negative control and Dermabond as the positive control. These data points can be lumped into three distinct groups during statistical analysis which are as follows:

Group 1: Dermabond

Group 2: Cyanoacrylate Ester, Bilayer Medhesive-054/30 Wt % PCL

Group 3: Medhesive-054, Medhesive-061, and Tisseal

This data demonstrates that these blended bilayer formulations are statistically the same as cyanoacrylate ester, also known as crazy glue.

4.5. Lap Shear Testing Comparison of Blending Trilayer Formulations Using PVA and PCL.

Figure 7:
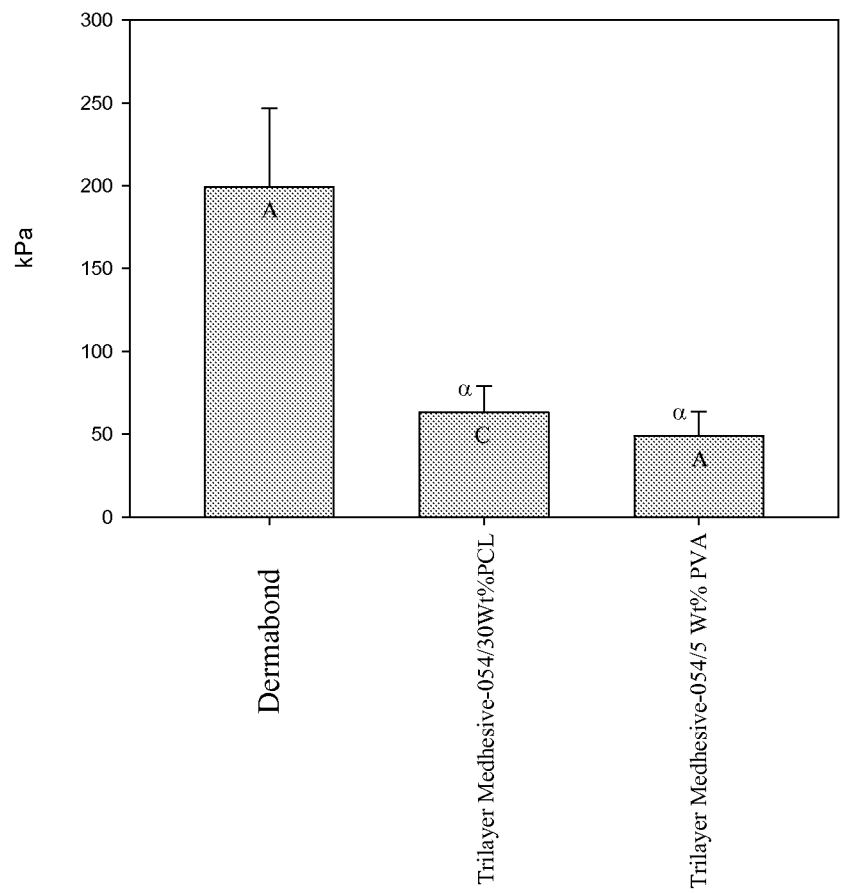
FIG. 7 depicts the peak stress required to separate two pieces of adhered collagen sheets in lap shear mode. Mode of failure: A=Adhesive failure; C=Cohesive failure. $\alpha$=statistically different from Dermabond. ($p$=0.05).
Figure 8:
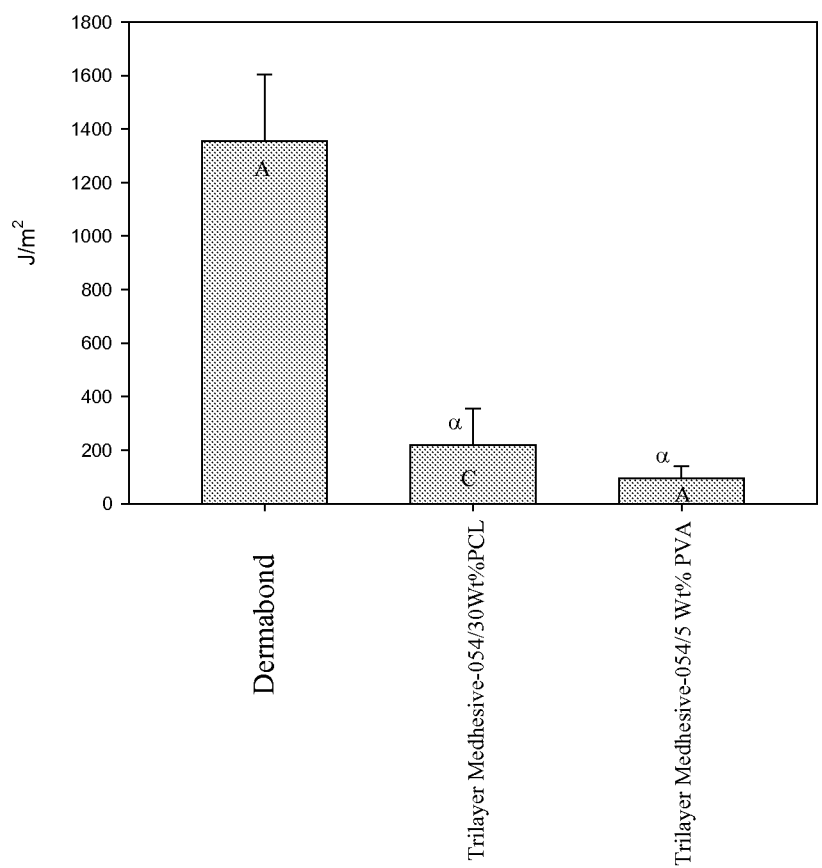
FIG. 8 provides a graphical representation of the work of adhesion required to separate two pieces of adhered collagen sheets in lap shear mode. Mode of failure: A=Adhesive failure; C=Cohesive failure. $\alpha$=statistically different from Dermabond. ($p$=0.05).
Figure 9:
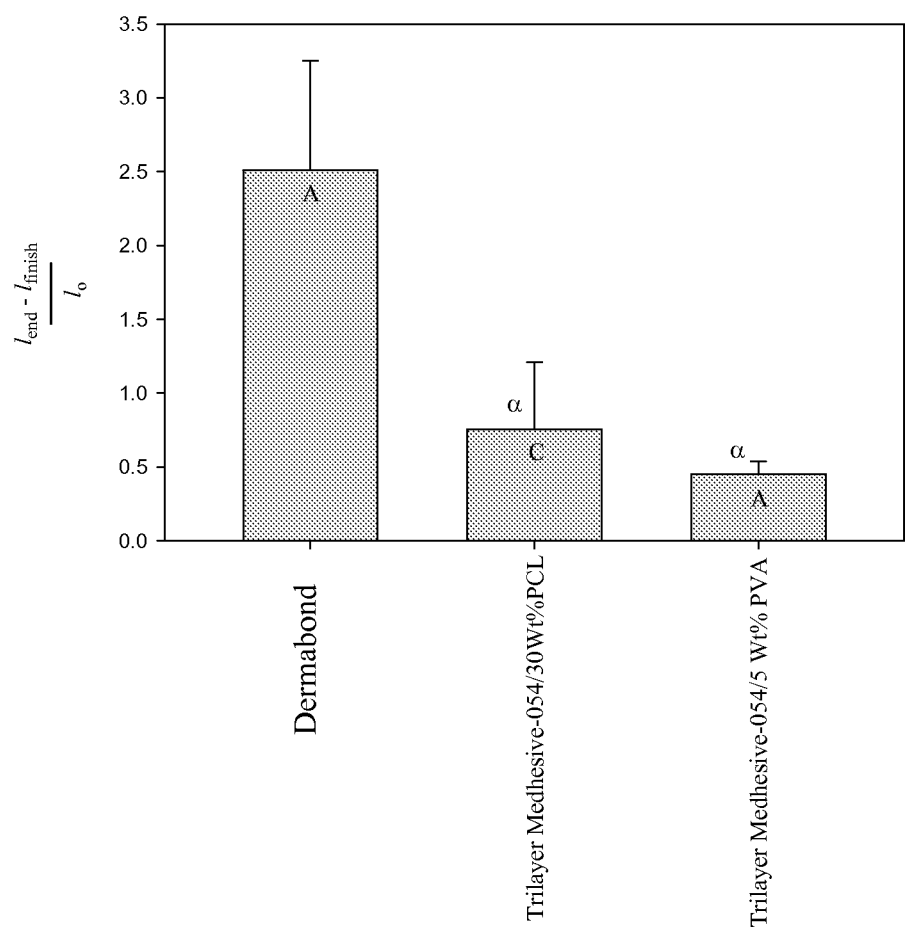
FIG. 9 shows strain at failure for two pieces of adhered collagen sheets separated via lap shear mode. Mode of failure: A=Adhesive failure; C=Cohesive failure. $\alpha$=statistically different from Dermabond. ($p$=0.05).

The data shown in FIGS. 7, 8 and 9 demonstrates the influence of using a trilayer formulation with PCL-triol or PVA. All data was stopped when the adhesive had lost 99% of its strength meaning it was possible to accurately calculate the energy needed to break the adhesive bond as well as the failure strain. The results show that blended thin-film adhesives are statistically different than Dermabond in all categories. Trilayer of Medhesive-054/5 Wt % PVA failed at the bovine pericardium backing-adhesive interface. It may be possible to add more Medhesive-054 in the first coating to create better adhesion. Overall, the relative amounts with each layer should be optimized to achieve maximum adhesive and cohesive properties.

4.6. Lap Shear Testing Comparison of Blending Trilayer Formulations Using PVA.

Figure 10:
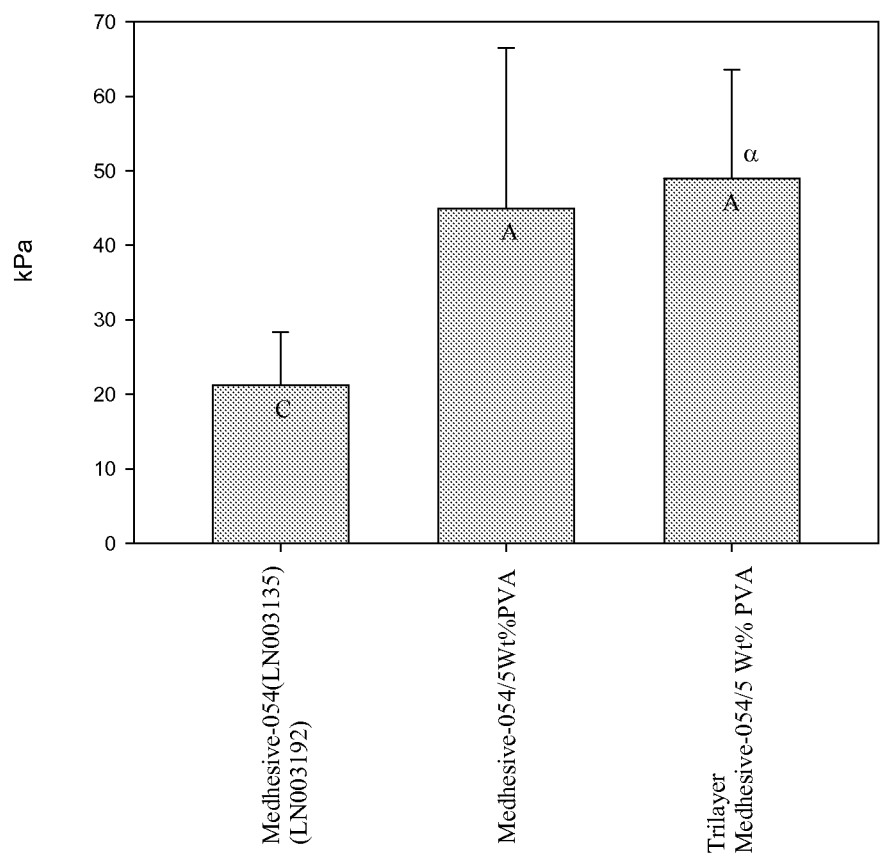
FIG. 10 depicts peak stress required to separate two pieces of adhered collagen sheets in lap shear mode. Mode of failure: A=Adhesive failure; C=Cohesive failure. $\alpha$=statistically different from Medhesive-054. ($p$=0.05).

The results shown in FIG. 10 that the amount of stress that can be achieved is not statistically different for the trilayer blending versus the blending formulation. However, there is a statistical difference between the unblended Medhesive-054 and the trilayer coating. Improvements may be possible by increasing or decreasing the amount of Medhesive-054 or PVA in any of the three layers.

4.7 Burst Strength Tests Performed Using Strattice as Backing Material 72 mg of Medhesive-054 in 4 mL of methanol was coated onto Strattice, a dermal allograft from Lifecell corporation, and dried. Burst strength test was performed as specified above, using bovine pericardium as the test substrate. A burst pressure of 326+/−54 mmHg was recorded.

5.1 Results for Surphys-029
5.2 Formation of Surphys-029 Hydrogel

Surphys-029 was dissolved in phosphate buffered saline (PBS, pH 7.4, at two times the normal concentration) at 300 mg/mL. The polymer solution was mixed with equal volume of $NaIO_4$ (12-48 mM) solution in a test tube lightly agitated. When the polymeric solution ceased to flow, the solution was considered fully cured. Table I shows that the minimum curing time occurs at around 28 seconds at a periodate:DOHA molar ratio of 0.33 to 0.5. This result demonstrated that Surphys-029 can cure rapidly and can potentially be used as an in situ curable tissue adhesive or sealant.

TABLE I

Curing Time of Surphys-029

| Periodate:DOHA Molar Ratio | Curing Time (s) |
|---|---|
| 1.00 | 150 |
| 0.75 | 50 |
| 0.66 | 37 |
| 0.50 | 28 |
| 0.33 | 28 |
| 0.25 | 38 | least one hour. The samples were further dried in a vacuum desiccator for at least 24 hours.

Burst Strength Adhesion Testing

Figure 13:
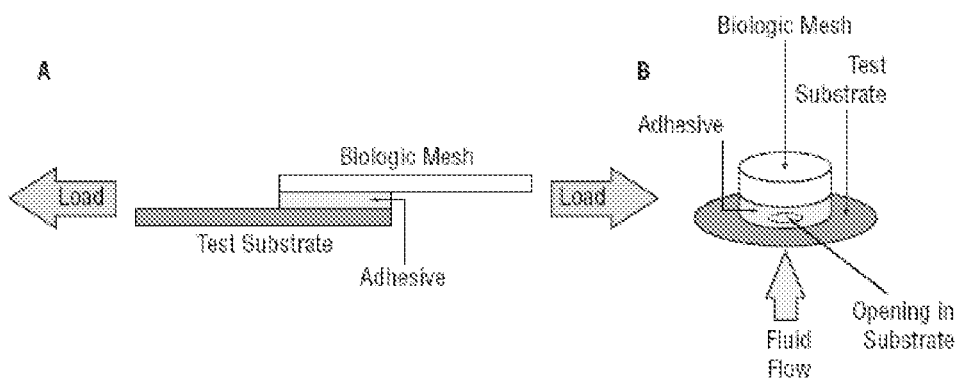
FIG. 13 is a depiction of. schematics of A) lap shear and B) burst strength test setups.
Figure 14:
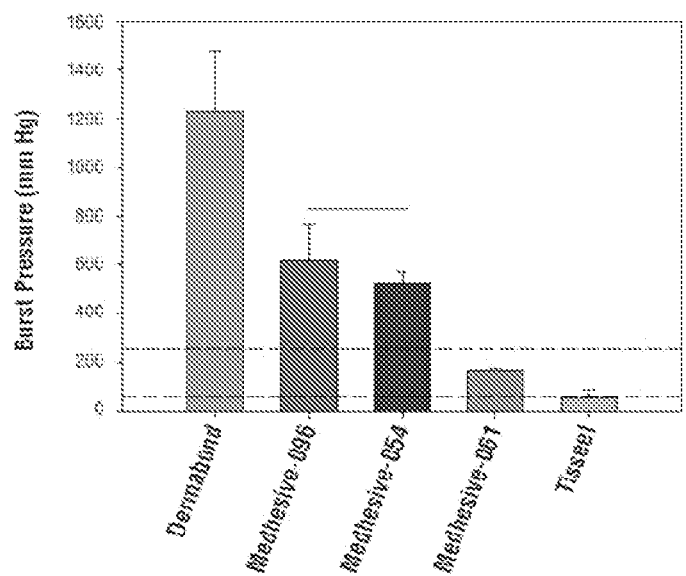
FIG. 14 shows the pressure required to burst through the adhesive joint sealed with adhesive-coated bovine pericardium. Dashed lines represent reported abdominal pressure range. Solid line represents statistical equivalence ($p>0.05$).

Procedures from American Society for Testing and Materials (ASTM) standards were used to perform burst strength (ASTM F2392) adhesion tests (FIG. 13). The adhesive coated-mesh was cut into 10-15 mm-diameter circular samples for burst strength tests. The test substrates (bovine pericardium) were shaped into 40 mm-diameter circles with a 3 mm-diameter defect at the center. A solution of $NaIO_4$ (40 μL) was added to the adhesive on the coated mesh prior to bringing the adhesive into contact with the test substrate. The adhesive joint was compressed with a 100 g weight for 10 min, and further conditioned in PBS (37° C.) for another hour prior to testing. A typical sample size was 6 in each test condition. Statistical assessment was performed using an analysis of variance (ANOVA), pair-wise comparisons with the Tukey test, and a significance level of 0.05. The adhesive properties of the bioadhesive constructs were determined and compared to controls: Dermabond®, Tisseel™, and Medhesive-061 (a Nerites liquid tissue adhesive). As seen in FIG. 14, Dermabond exhibited the highest adhesive strengths, and Medhesive-054 and Medhesive-096 significantly outperformed Medhesive-061 and Tisseel.

Lap Shear Adhesion Testing

Lap shear adhesion tests was performed using ASTM procedures (ASTM F2392) (FIG. 13). The adhesive coated-mesh was either cut into 2.5 cm×5 cm strips for lap shear tests. The test substrates (bovine pericardium) were shaped into 2.5 cm×5 cm strips. A solution of $NaIO_4$ (40 μL) was added to the adhesive on the coated mesh prior to bringing the adhesive into contact with the test substrate. The adhesive joint was compressed with a 100 g weight for 10 min, and further conditioned in PBS (37° C.) for another hour prior to testing. A typical sample size was 6 in each test condition. Statistical assessment was performed using an analysis of

5.3 Surphys-029 as an Anti-Fouling Coating

The substrate surfaces were cleaned by 10 minute sonication in 2-propanol. Test materials were coated with antifouling polymer by immersion in 1 mg/mL of Surphys-029 (0.3M $K_2SO_4$ 0.05M MOPS) for 24 hrs at 50° C. After coating, samples were rinsed twice with deionized water and dried in a stream of nitrogen gas.

Figure 11:
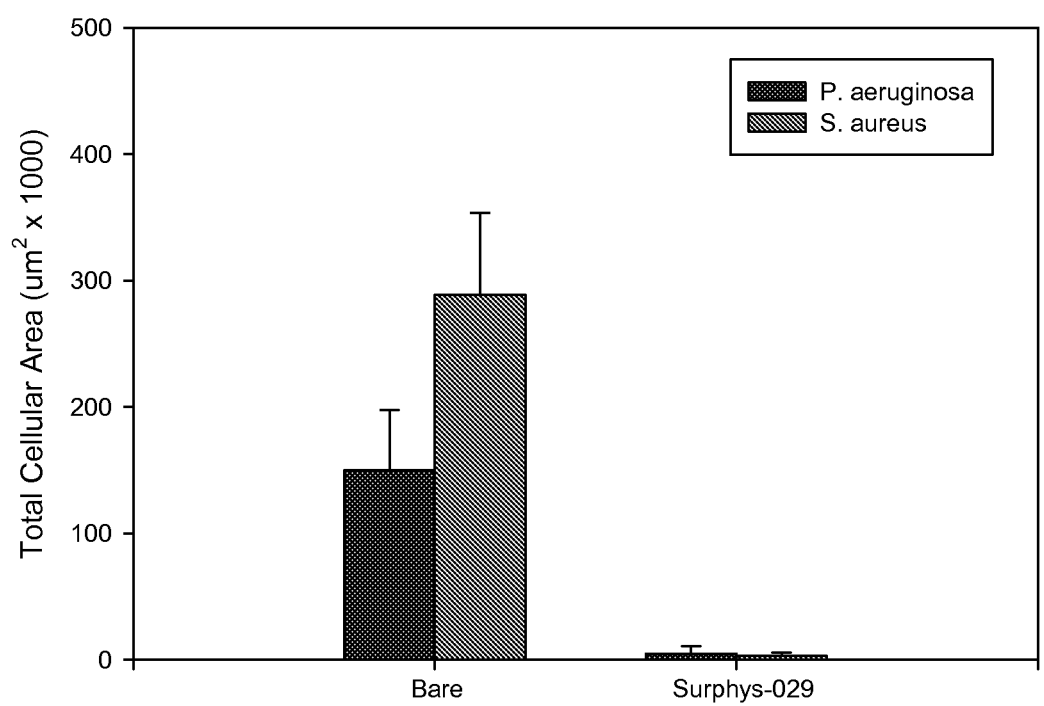
FIG. 11 shows bacterial adhesion on coated PVC.
Figure 12:
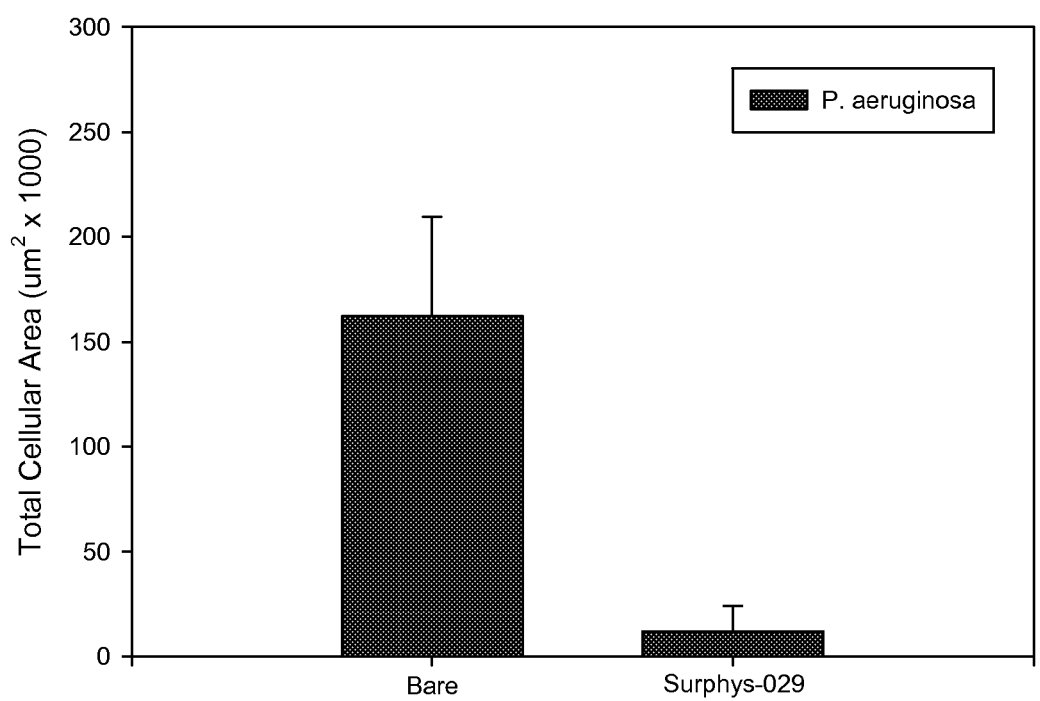
FIG. 12 shows bacterial adhesion on coated Acetal.

To determine the antifouling ability of these coatings, bacterial cell attachment and biofilm formation was assessed on both coated and uncoated samples. These surfaces were incubated with bacteria ($1 \times 10^8$ CFU/mL) in tryptic soy broth (TSB) in a 12-well cell culture plate for 4 hrs at 37° C. After which, each surface was rinsed three times with sterile PBS. The attached bacteria cells were stained with Syto 9 and 9 images per surfaces were capture using epifluorescence microscope. The total coverage of adhered bacteria cells on both PVC and acetal surfaces are shown in FIGS. 11 and 12. It was demonstrated that Surphys-029 coated surfaces demonstrated reduced the amount of bacteria attachment as compared to the uncoated surfaces.

Coating of Adhesive Polymer onto Biologic Mesh

To coat the adhesive film onto bovine pericardium, a hydrated segment of biologic mesh was placed in a template of the same size (typically 91 mm×91 mm). A polymer solution (15-120 mg/mL) in methanol or chloroform was added and allowed to slowly evaporate in a 37° C. oven for at variance (ANOVA), pair-wise comparisons with the Tukey test, and a significance level of 0.05.

Figure 15:
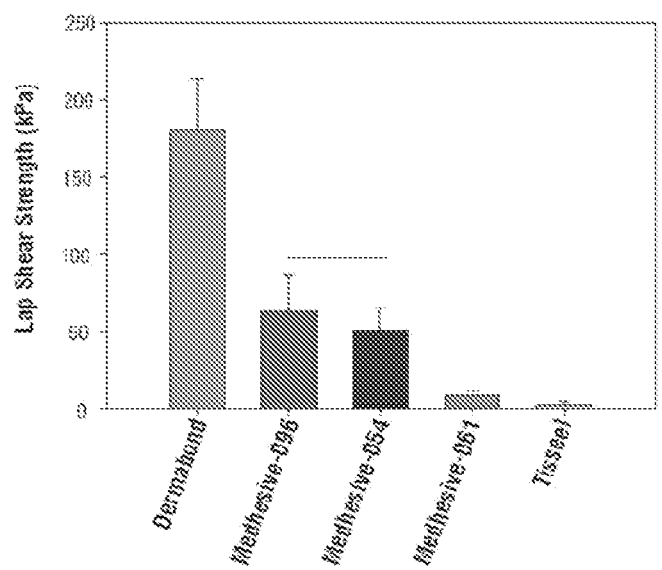
FIG. 15 shows the lap shear adhesive strength required to separate the adhesive joint formed using adhesive-coated bovine pericardium. Solid line represents statistical equivalence ($p>0.05$).

The adhesive properties of the bioadhesive constructs were determined and compared to controls: Dermabond®, Tisseel™, and Medhesive-061 (a Nerites liquid tissue adhesive). For both lap shear adhesion tests (FIG. 15), Dermabond exhibited the highest adhesive strengths, and Medhesive-054 and Medhesive-096 significantly outperformed Medhesive-061 and Tisseel.

Effect of Periodate Concentration on Adhesive Properties

Using Medheisve-054 coated on bovine pericardium, $NaIO_4$ concentration was varied between 10-40 mg/mL. Lap shear adhesion test was performed as described above using bovine pericardium as the test substrate. As demonstrated in Table 2, both lap shear adhesion strength and work of adhesion, the total amount of energy required to separate the adhesive joint, increased with increasing $NaIO_4$ concentration, but exhibited no further increase when the concentration exceeded 20 mg/mL.

TABLE 2

| $NaIO_4$ Concentration (mg/mL) | Maximum strength (kPa) | Work of adhesion (J/m$^2$) [%] | Strain at Failure |
|---|---|---|---|
| 10 | 9.34 ± 2.89 * | 22.2 ± 12.3 [$] | 0.469 ± 0.439 |
| 20 | 46.6 ± 19.3 | 77.0 ± 26.1 [$] | 0.366 ± 0.0696 |
| 30 | 42.3 ± 25.1 | 60.7 ± 34.5 | 0.315 ± 0.0627 |
| 40 | 45.0 ± 20.4 | 60.8 ± 14.6 | 0.168 ± 0.118 |

TABLE 2-continued

| NaIO$_4$ Concentration (mg/mL) | Maximum strength (kPa) | Work of adhesion (J/m$^2$) % | Strain at Failure |
|---|---|---|---|

Performed using Medhesive-054-coated bovine pericardium
% Normalized by initial area of contact
* Significantly different from other test articles (p < 0.05)
$ Significantly different from each other (p < 0.05)

Effect of Polymer Loading Density on Adhesive Properties

Using Medheisve-054 coated on bovine pericardium, the effect of polymer loading density (15-90 mg/mL) on the adhesive properties of the construct was determined. Lap shear adhesion test was performed as described above using bovine pericardium as the test substrate. As shown in Table 3, higher loading density yielded higher adhesive strengths for both lap shear and burst tests.

TABLE 3

| Loading Density (g/m$^2$) | Maximum Strength (kPa) | Work of adhesion (J/m$^2$) % | Strain at failure | Burst Pressure (mm Hg) |
|---|---|---|---|---|
| 15 | 18.9 ± 5.41 | 33.2 ± 5.48 | 0.432 ± 0.201 | — |
| 30 | 31.7 ± 12.5 | 77.9 ± 35.5 | 0.494 ± 0.0997 | 219 ± 116 |
| 60 | 42.5 ± 12.3 | 91.6 ± 24.1 | 0.428 ± 0.0684 | 422 ± 136 |
| 90 | 37.9 ± 11.5 | 94.4 ± 42.2 | 0.422 ± 0.0543 | 495 ± 174 |

Performed using Medhesive-054-coated bovine pericardium
% Normalized by initial area of contact
Vertical lines = statistically equivalent; p > 0.05

Effect of Contact Time on Adhesive Properties

Using Medheisve-054 coated on bovine pericardium, the effect of contact time on the adhesive properties of the construct was determined. Lap shear adhesion test was performed as described above using bovine pericardium as the test substrate. As demonstrated in Table 4, the adhesive joint had already reached maximum strength after merely 10 min of contact.

TABLE 4

| Contact Time (min) | Maximum Strength (kPa) | Work of adhesion (J/m$^2$) % | Strain at failure |
|---|---|---|---|
| 10 | 62.0 ± 23.2 | 89.4 ± 42.1 | 0.324 ± 0.137 |
| 70 * | 60.6 ± 33.0 | 115 ± 43.6 | 0.479 ± 0.0892 |
| 120 * | 55.7 ± 19.4 | 70.0 ± 21.5 | 0.332 ± 0.0361 |
| 180 * | 58.2 ± 16.8 | 134 ± 79.9 | 0.516 ± 0.155 $ |

Performed using Medhesive-054-coated bovine pericardium
% Normalized by initial area of contact
* Submerged in PBS at 37° C. for the final 60 min before testing
$ Statistically higher than 10-min contact time (p < 0.05)

Effect of Patterning on Adhesive Properties

Figure 16:
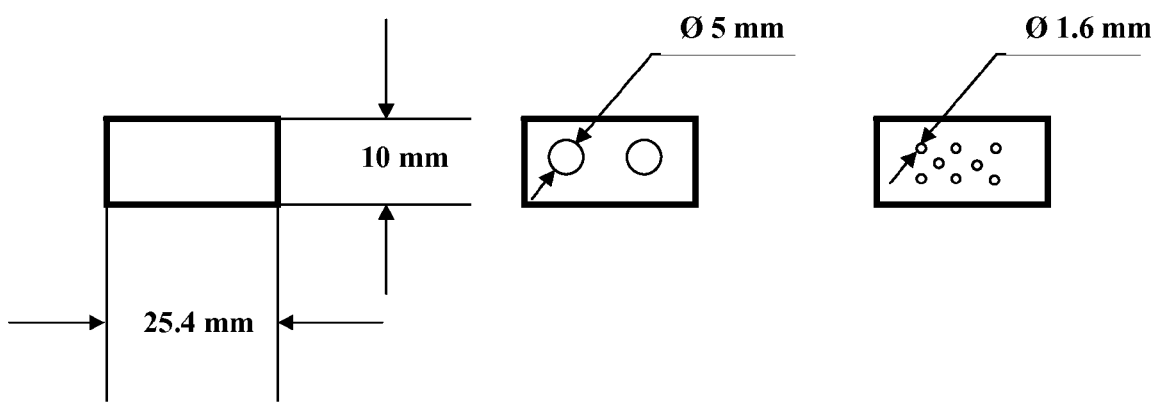
FIG. 16 provides schematics of A) control construct with 100% area coverage, B) a patterned construct with 8 circular uncoated areas (diameter=1.6 mm), and C), a patterned construct with 2 circular uncoated areas (diameter=0.5 mm).

Medheisve-096 (60 g/m$^2$) was coated on bovine pericardium with circular uncoated areas to determine the effect of patterning on the adhesive properties of the bioadhesive construct (FIG. 16). Lap shear adhesion test was performed as described above using bovine pericardium as the test substrate. As demonstrated in Table 5, the adhesive strength in general decreased with decreased areas of uncoated regions.

TABLE 5

| Percentage of Area Coated with Adhesive | Maximum Strength (kPa) | | Patterned Feature | |
|---|---|---|---|---|
| | Average | St Dev. | Diameter (mm) | Number of Features |
| 100% | 107.5 | 24.7 | — | — |
| 95.5% | 86.6 | 13.3 | 1.6 | 8 |
| 84.5% | 70.0 | 8.10 | 5 | 2 |

Effect of Oxidant Delivery Method on Adhesive Properties

The effect of different oxidant delivery methods was studied by testing lap shear adhesion strengths of Medhesive-054 (120 g/m$^2$) coated on Permacol®. Lap shear adhesion test was performed as described above using bovine pericardium as the test substrate. For the brush method, a solution of 40 μL of 20 mg/mL of NaIO$_4$ was brushed onto the substrate prior to forming the adhesive joint. For the spray method, NaIO$_4$ solution (20 mg/mL) was sprayed on the construct prior to contact with the substrate. For the dipping method, the construct was dipped into a 20 mg/mL NaIO$_4$ solution prior to forming the adhesive joint. Results from the lap shear adhesion test can be seen in Table 6.

TABLE 6

| Delivery Method | Max Strength (kPa) | | Failure Strain | | Work of Adhesion (J/m$^2$) | |
|---|---|---|---|---|---|---|
| | Avg | St. Dev. | Avg | St. Dev. | Avg | St. Dev. |
| Brush | 71.0 | 12.2 | 0.406 | 0.114 | 128 | 71.7 |
| Spray | 94.2 | 4.19 | 0.352 | 0.0695 | 132 | 44.0 |
| Dip | 70.4 | 16.9 | 0.301 | 0.0692 | 89.2 | 44.8 |

Adhesive Coated on Commercially Available Hernia Meshes

Figure 17:
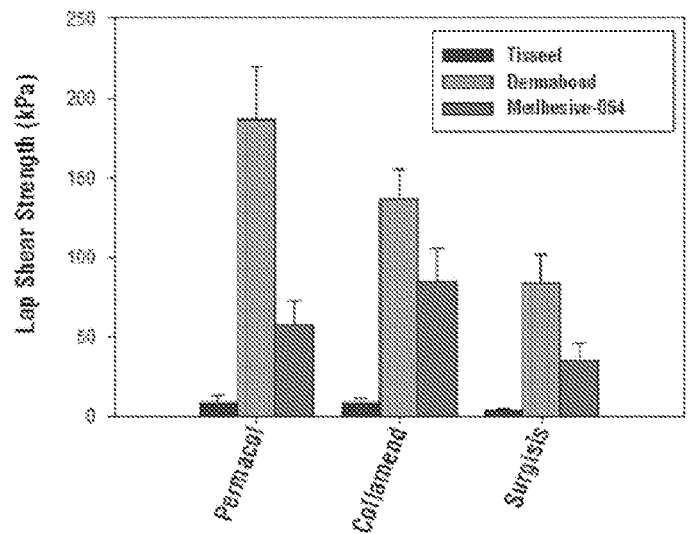
FIG. 17 provides the lap shear adhesive strength required to separate the adhesive joint formed using adhesive-coated bovine pericardium.

Three commercially available biologic meshes, two crosslinked porcine dermal tissues, Permacol™ and Colla-Mend™, and a multi-layered porcine small intestinal submucosal tissue, Surgisis™, were coated with Medhesive-054. Lap shear adhesion tests were performed using hydrated bovine pericardium as the test substrate. Although Dermabond exhibited the highest shear strength, meshes fixed with cyanoacrylate were reported to have reduced tissue integration combined with pronounced inflammatory response. Additionally, cyanoacrylate adhesive significantly reduced the elasticity of the mesh and abdominal wall, and impaired the biomechanical performance of the repair. Due to the release of toxic degradation products (formaldehyde), cyanoacrylates are not approved for general subcutaneous applications in the US. Medhesive-054 combined with all mesh types outperformed Tisseel by seven- to ten-fold (FIG. 17). Even with relatively weak adhesive strengths, fibrin-based sealants have demonstrated at least some level of success in mesh fixation in vivo, which suggests that Nerites' bioadhesive constructs have sufficient adhesive properties for hernia repair. While the Medhesive-054 constructs only exhibited adhesive strengths that were 30-60% of those of Dermabond, it is possible to further optimize the coating technique or adhesive formulation for each mesh type.

Effect of Sterilization on Adhesive Properties

Medhesive-054 (120 g/m$^2$)-coated Permacol™ was sterilized with electron beam (E-beam) irradiation (15 kGy) and it adhesive properties was compared with a non-sterile construct. Lap shear adhesion test was performed as described above using bovine pericardium as the test substrate. As shown in Table 7, E-beam did not have any effect on the adhesive properties on the bioadhesive construct.

TABLE 7

| Delivery Method | Max Strength (kPa) | | Failure Strain | | Work of Adhesion (J/m$^2$) | |
|---|---|---|---|---|---|---|
| | Avg | St. Dev. | Avg | St. Dev. | Avg | St. Dev. |
| None Sterile | 71.0 | 12.2 | 0.406 | 0.114 | 128 | 71.7 |
| E-beam Treated | 86.3 | 35.3 | 0.361 | 0.0680 | 139 | 93.2 |

Burst Strength of Adhesive Coated on Commercially Available Biologic Mesh

Burst strength adhesion test (ASTM F2392) was performed on Medhesive-054 (46 g/m$^2$)-coated Strattice®, a porcine dermis mesh, using bovine pericardium as the test substrate. The average maximum pressure was found to be 326±54.4 mmHg.

Adhesive Coated on Commercially Available Dural Meshes

Burst strength adhesion test (ASTM F2392) was performed on Medhesive-096 (90 g/m$^2$)-coated SyntheCel®, a sheet formed from cellulose fibers, using bovine pericardium as the test substrate. The average maximum pressure was found to be 412.±78.9 mmHg.

Sealing of Small Intestine

Bovine small intestines were rinsed and cut into 6" segments. A small incision was made near the center with a #11 scalpel blade and sutured once with 5-0 nylon sutures. 37.1 uL of 20 mg/mL NaIO$_4$ solution was applied directly to the intestine around the defect and a 15 mm diameter bovine pericardium backing-coated with 60 g/m$^2$ of Medhesive-054 was applied over the defect. The adhesive joint was weighted down with a 100 g weight and allowed to cure for 10 min. The tissue was then hydrated for 1 hour in PBS at 37° C. and burst testing was performed by pumping air into the intestine at a rate of 20 mL/min until bubbles appeared from the defect. At which point the pressure was recorded. The average maximum pressure was found to be 49.4±19.2 mmHg.

Adhesive Coated on a Synthetic Mesh

A polymer solution in methanol or chloroform (70-240 mg/mL) was added onto a fluorinated-release liner and dried in a vacuum desiccator. A synthetic mesh was placed over the dried film and two glass plates were used to sandwich the construct while being held in place with paper binders. The material was put into a desicator which was vacuumed and refilled with Ar gas. The dedicator was incubated at 55° C. for 1 hour and cooled to room temperature prior to use. Lap shear adhesion test (ASTM F2255) was performed using bovine pericardium as the test substrate. For Medhesive-096 (240 mg/mL) coated on a Dacron™ mesh, values for maximum lap shear strength, strain at failure, and work of adhesion were found to be 69.3±9.82 kPa, 0.516±0.0993, and 174±13.8 J/m$^2$, respectively, with n=5.

Adhesive Coated on a Titanium Surface

Titanium (Ti)-coated silicon slides with a dimension of ½ in.×1½ in. were cleaned in four solvents 5% Contrad solution, H$_2$O, acetone, and isopropanol sequentially in a sonication bath and then treated with oxygen plasma for 5 minutes. 54.4 µl of Medhesive-096 (70 mg/mL) solution in chloroform was dropped onto the end of the Ti slide in a ½ ins X 1 cm area, and the solvent were allowed to evaporate. 40 µl of 20 mg/ml of NaIO$_4$ was brushed onto one adhesive-coated slide and, which was brought into contact with another adhesive-coated slide to form an adhesive joint, which was weighted down by a 100 g weight for 2 hours. Lap shear adhesion test (ASTM D1002) was performed on the adhesive joint and values for maximum strength, strain at failure, and work of adhesion were found to be 307 kPa, 0.90, and 360 J/m$^2$, respectively.

Effect of Blending on Adhesive Properties

To form an adhesive coating blend, Medhesive-054 with PCL-triol (MW=900, 0-30 wt %) was dissolved in methanol (60 g/m$^2$) and coated onto bovine pericardium as previously described. Lap shear adhesion test was performed as described above using bovine pericardium as the test substrate. As shown in Table 8, both maximum lap shear strength and strain at failure did not change statistically. However, at elevated PCL-triol content (30 wt %), the work of adhesion was nearly doubled (p<0.05).

TABLE 8

| Wt % PCL-triol | Lap Shear Strength (kPa) | | Strain at Failure | | Work of Adhesion (J/m$^2$) | |
|---|---|---|---|---|---|---|
| | Avg. | St. Dev. | Avg. | St. Dev. | Avg. | St. Dev. |
| 0 | 70.0 | 9.50 | 0.293 | 0.0498 | 77.7 | 13.3 |
| 5 | 65.6 | 18.8 | 0.358 | 0.0519 | 99.4 | 15.6 |
| 15 | 88.4 | 20.1 | 0.469 | 0.191 | 117 | 15.8 |
| 25 | 61.3 | 20.3 | 0.410 | 0.100 | 95.9 | 35.3 |
| 30 | 74.6 | 29.3 | 0.481 | 0.160 | 131* | 51.2 |

Effect of Blending on Adhesive Film Degradation

Adhesive films were incubated in PBS at 55° C. and it mass loss over time was recorded. Medhesive-054 films lost over 26.2±3.21 wt % of its original mass after 31 days of incubation. When blended with PCL-triol (30 wt %), mass loss was accelerated, demonstrating 34.5±3.73 wt % loss in only 24 days. However, blending with 5 wt % polyvinyl alcohol (PVA) did not result in changes in the rate of film degradation (22.5±1.11 wt % mass loss over 35 days).

Adhesive Coated on a Synthetic Mesh

A polymer solution in methanol or chloroform (240 mg/mL) was added onto a fluorinated-release liner and dried in a vacuum dessicator. A synthetic mesh was placed over the dried film and two glass plates were used to sandwich the construct while being held in place with paper binders. The material was put into a dessicator which was vacuumed and refilled with Ar gas. The desicator was incubated at 55° C. for 1 hour and cooled to room temperature prior to use. Lap shear adhesion test (ASTM F2255) was performed using bovine pericardium as the test substrate and the lap shear strength and work of adhesion of construct coated on Dacron™ and polypropylene meshes are shown in Table 9.

TABLE 9

Lap shear adhesion test results of adhesive-coated synthetic meshes.

| Adhesive Polymer | Mesh Type | Maximum Strength (kPa) | Work of Adhesion (J/m$^2$) |
|---|---|---|---|
| Medhesive-096 | Dacron | 69.3 ± 9.80 | 174 ± 13.8 |
| Medhesive-112 | Dacron | 44.2 ± 32.2 | 154 ± 128. |
| Medhesive-054 | Polypropylene PPKM404 | 46.0 ± 15.6 | 81.6 ± 47.8 |
| Medhesive-054 | Polypropylene PPKM602 | 45.6 ± 21.2 | 145 ± 33.6 |
| Medhesive-054 | Polypropylene PPKM802 | 26.1 ± 10.2 | 76.8 ± 35.6 |
| Medhesive-054 | Polypropylene PPKM802 | 30.3 ± 17.0 | 47.5 ± 32.3 |
| Medhesive-096 | Polypropylene PPKM802 | 33.9 ± 13.0 | 36.4 ± 19.1 |

Patterned Adhesive Coating of Mesh for Accelerated Mesh-Tissue Integration

Figure 18:
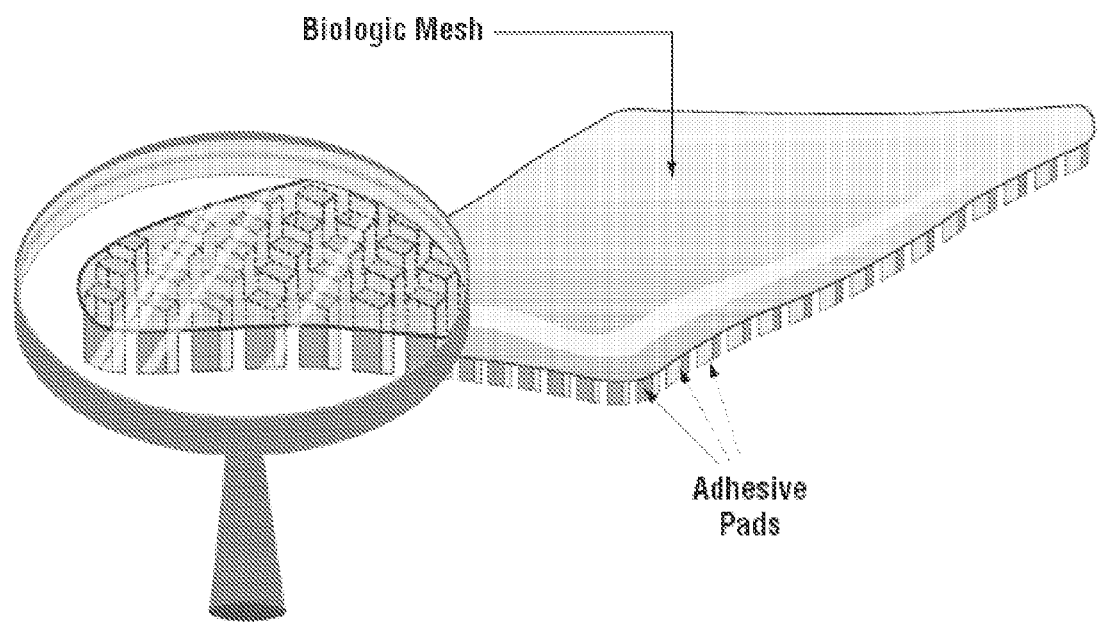
FIG. 18 provides a mesh coated with adhesive pads.
Figure 19:
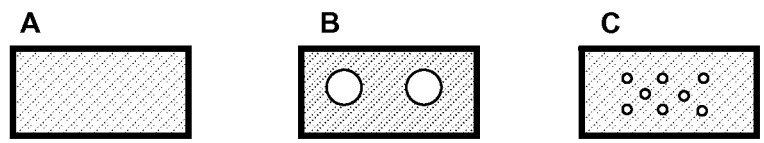
FIG. 19 provides chematics of A) construct with 100% area coverage, B) a patterned construct with 2 circular uncoated areas with larger diameter, and C), a patterned construct with 8 circular uncoated areas with smaller diameter.

The adhesive polymer can be coated on the mesh in a pattern to promote faster integration of the host tissue and mesh. Unlike other fixation methods, adhesives may act as a barrier for tissue ingrowth into the mesh if their degradation rate is slower than the cell invasion rate and subsequent graft incorporation. Meshes secured with a slow degrading adhesive such as cyanoacrylate demonstrated impaired tissue integration. For meshes secured with conventional methods, the tensile strength of the mesh-tissue interface reached a maximum within four weeks after implantation, indicating that the meshes were fully integrated with the host tissue. This suggests that cellular infiltration occurs earlier. While the adhesive polymers of the invention exhibit a variety of degradation profiles, some formulations may take several months to be completely absorbed. To ensure rapid tissue integration into the mesh while maintaining strong adhesion at the time of implantation, adhesives can be coated onto a mesh in an array of adhesive pads, leaving other areas of the mesh uncoated as shown in FIG. 18. Other patterns with various geometric shapes (circular, rectangular, etc.) can also be created FIG. 19. The regions coated with adhesive will provide the initial bonding strength necessary to secure the mesh in place, while the uncoated regions will provide an unobstructed path for cellular invasion and tissue ingrowth to immediately occur.

To create a patterned adhesive polymer coating, a solvent casting method could be used, in which a metallic lattice will be placed over the mesh while the polymer solution is drying. The lattice will be used to displace the polymer solution so that an uncoated region is formed as the solution dries. By controlling the dimensions (5-10 mm) and the thickness (0.2-1.0 mm) of the lattice, it is possible to vary the ratio of the surface areas of the coated and uncoated regions. Bovine pericardium will be used both as the surrogate backing and test substrate. Lap shear adhesion testing will be performed to determine the effect of the patterned coating on the adhesive properties of the bioadhesive construct. For each coating pattern, a minimum of 10 repetitions will be tested, and statistical analysis will be performed using ANOVA, the Tukey post hoc analysis, and a significance level of p=0.05.

It is expected that a patterned adhesive can be easily achieved using the described method. The adhesive strength of the patterned coating will likely be slightly lower compared to the non-patterned adhesive coating since the overall surface area of the adhesive is decreased. By varying the ratio of the surface areas between the coated and uncoated regions, the surface can be tailored adjust for the initial adhesive strength to the rate of tissue ingrowth. A pattern that results in greater than 80% of the adhesive strength of the non-patterned coating will be selected for subsequent animal studies. The rate of tissue ingrowth will be determined by implanting both patterned and non-patterned bioadhesive constructs into a rabbit model.

Characterization of the Adhesive Polymer Films

For the purpose of testing in this experiment, adhesive polymers were cast into films by the slow evaporation of methanol or chloroform in a mold (referred to as adhesive films in this proposal). Their percent swelling, tensile mechanical properties, and in vitro degradation profiles were then determined. For each test, the films were cured by the addition of a sodium periodate ($NaIO_4$) solution. Additionally, PCL-triol (30 wt %) was formulated into the adhesive film to determine the effect of added PCL content on the physical and mechanical properties of the adhesives. The equilibrium swelling of the adhesive films in phosphate buffered saline (PBS, pH 7.4, 37° C., 24 hours) was calculated by the equation, $(W_s-W_i)/W_i$, where $W_i$ and $W_s$ are the weights of the dry and swollen films measured before and after the swelling experiment, respectively. As shown in Table 10, the degree of swelling is affected by the composition of the adhesive formulation, as well as by the loading density (mass of polymer per unit area of the mold) of the films. For example, higher PCL content in Medhesive-096 (21 wt %) resulted in less swelling compared to Medhesive-054 (13 wt %). When PCL-triol was added to both polymers, these formulations exhibited significantly less swelling. These observations were expected since the extent of water uptake is related to the hydrophobicity of the films. In addition to PCL content, the polymer loading density also affected the extent of swelling, with films formed with half the loading density absorbing 1.4 times more water. The loading density likely affected the crosslinking density of the film, which is inversely proportional to the degree of swelling.

TABLE 10

| Adhesive Polymer | Loading Density $(g/m^2)$ # | Weight % PCL | Swollen film thickness (m) $ | Extent of Swelling $(W_s - W_i/W_i)$ * |
|---|---|---|---|---|
| Medhesive-054 | 23 | 0 | 263 ± 9.64 | 9.8 ± 0.90 |
| | 46 | 0 | 368 ± 4.58 | 7.2 ± 0.61 |
| | 46 | 30 | 260 ± 40.1 | 4.2 ± 0.50 |
| Medhesive-096 | 23 | 0 | 189 ± 4.51 | 7.0 ± 0.20 |
| | 46 | 0 | 261 ± 11.9 | 5.0 ± 0.20 |
| | 46 | 30 | 209 ± 6.66 | 4.2 ± 0.20 |

Amount of polymer used to form the dry film in mass per unit area of the mold;

$ Measured with micrometer;

* For each polymer type, the mean values for each test article are significantly different from each other ($p < 0.05$)

Determination of the tensile mechanical properties of the adhesives was based on American Society for Testing and Materials (ASTM) D638 protocols. Tensile tests on dog-bone shaped films (9.53 mm gauge length, 3.80 mm gauge width, and 12.7 mm fillet radius, swollen in PBS (pH 7.4) for 1 hr) were performed and the maximum tensile strength was measured. Both the Young's modulus and toughness were also determined, based on the initial slope and area under the stress-strain curve, respectively. As shown in Table 11, the mechanical properties of the film were strongly affected by the PCL content. For example, Medhesive-096 demonstrated significantly higher tensile strength and toughness (251±21.2 kPa, and 266±29.1 $kJ/m^3$, respectively), compared to Medhesive-054 (168±31.0 kPa and 167±38.6 $kJ/m^3$). Strength and toughness values for Medhesive-096 formulated with the addition of 30 wt % of PCL-triol were even greater (357±37.5 kPa and 562±93.1 $kJ/m^3$, respectively), suggesting that the mechanical properties of these adhesives can be modulated by blending them with compounds that impart the desired characteristics. Note that the toughness more than doubled with the addition of PCL-triol to Medhesive-096. Elevated film toughness has been found to strongly correlate to high lap shear adhesion strength. The addition of PCL-triol probably increased the crosslinking density in the film, which resulted in the observed increase in mechanical properties. This increase in crosslinking density did not result in brittle films as shown in the elevated strain values.

TABLE 11

| Adhesive polymer | Weight % PCL | Young's modulus (kPa) | Maximum strength (kPa) | Strain at failure | Toughness (kJ/m$^3$) |
|---|---|---|---|---|---|
| Medhesive | 0 | 142 ± 37.6 | 168 ± 31.0 | 1.70 ± 0.403 | 168 ± 38.6 |
| -054 | 30 | 103 ± 57.7 | 135 ± 51.6 | 1.95 ± 0.491 | 162 ± 77.3 |
| Medhesive | 0 | 219 ± 40.8 | 251 ± 21.2 | 1.82 ± 0.217 | 266 ± 29.1 |
| -096 | 30 | 235 ± 58.1 | 357 ± 37.5 | 2.73 ± 0.337 | 562 ± 93.1 |

Vertical lines = statistically equivalent; p > 0.05

Figure 20:
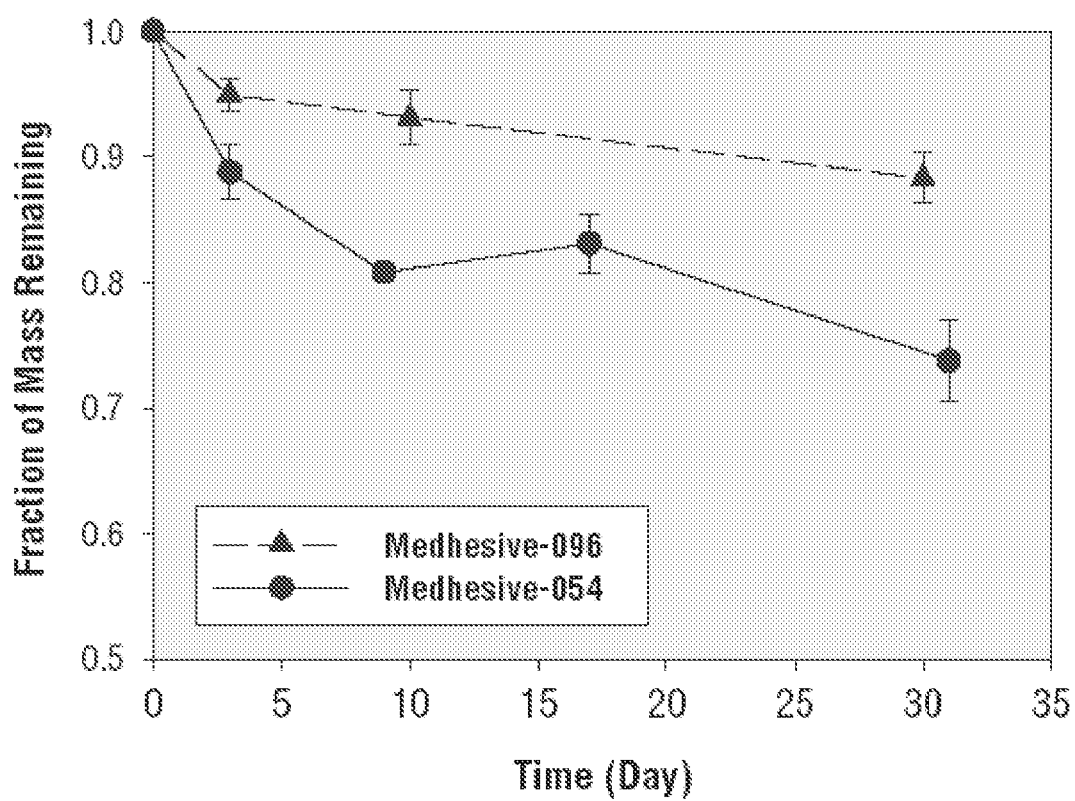
FIG. 20 shows degradation rate of Medhesive-096 and 054 at 55° C. in PBS.

The in vitro degradation was determined by monitoring the mass loss of the adhesive films incubated in PBS (pH 7.4) over time at 55° C. to accelerate the degradation process (FIG. 20). Medhesive-054 lost over 26±3.2% of its original dry mass over one month, while the more hydrophobic Medhesive-096 demonstrated a slower rate of degradation (12±2.0% mass loss). Hydrolysis was also performed at 37° C. where these films lost over 13±2.9% (Medhesive-054) and 4.0±2.3% (Medhesive-096) after 18 and 20 days of incubation, respectively. Since our adhesive films degrade mainly through hydrolysis, more water uptake by Medhesive-054 films (collaborated with elevated swelling) resulted in faster degradation. It is not clear whether degradation was accelerated at 55° C. due to a lower number of data points.

These results demonstrate that both the chemical architecture and adhesive formulation play a significant role in the physical and mechanical properties of the adhesive films. Specifically, the hydrophobicity of the film had a significant impact on the extent of swelling, which was found to be inversely proportional to the mechanical properties and rate of hydrolysis. By designing the adhesive polymers with different compositions, the polymers were able to be tailored for these properties, which were further refined by blending these polymers with PCL-triol.

Lap Shear Adhesion Strength of Adhesive Blends

The adhesive polymers Medhesive-096 or Medhesive-116 were coated on to bovine pericardium using the solvent casting method as described above. Solutions of the adhesive polymers were blended at the different concentrations and the mixture was applied to bovine pericardium as the backing material, and then allowed to dry slowly. Before forming the adhesive joint, a dilute solution of sodium periodate (NaIO$_4$, 20 mg/ml) was added to the pericardium substrate to oxidize the adhesives and lap shear testing was performed following ASTM F2255 protocols. Results for blends of Medhesive-096 and Medhesive-116 are shown in Table 12.

TABLE 12

Lap shear adhesion test results for adhesive blends (90 g/m$^2$) using bone tissue as the test substrate

| Weight % Medhesive-096 | Weight % Medhesive-116 | Maximum Adhesive Strength (kPa) | Strain at Failure | Work of Adhesion (J/m$^2$) |
|---|---|---|---|---|
| 75 | 25 | 67.3 ± 29.4 | 0.53 ± 0.10 | 158 ± 124 |
| 66 | 33 | 31.5 ± 15.0 | 0.42 ± 0.13 | 74.6 ± 32.7 |
| 50 | 50 | 27.2 ± 12.6 | 0.36 ± 0.10 | 56.7 ± 35.5 |
| 33 | 66 | 13.8 ± 5.47 | 0.25 ± 0.14 | 20.6 ± 13.4 |

Synthesis of 4-arm-PEG-PLA-MA Block Copolymer 24.8 g of 4-arm PEG-OH (MW 2,000), 50.0 g of L-lactide (LA), and 200 mL of toluene was added to a round bottom flask equipped with a Dean-Stark apparatus and a condensation column. The mixture was heated in an oil bath (155-165° C.) until 100 mL of toluene was evaporated with argon purging. The mixture was allow to cool to room temperature before 643 μL of tin(II) 2-ethylhexanoate was added. The mixture was stirred in an oil bath (155-165° C.) with argon purging for overnight. Polymer was purified by precipitation in diethyl ether two times. The dried polymer was further reacted with triethylamine (15.1 mL) and methacrylate anhydride (17.4 mL) in 300 mL of chloroform for overnight. The polymer was purified with ether precipitation, followed by washing with 12 mM HCl, saturated NaCl solution, and water. After additional ether precipitation, 23 g of polymer was obtained. From $^1$H NMR (400 MHz, CDCl$_3$/TMS), number of LA repeat per arm is 21.1 and the overall MW of the polymer is 8,400 Da.

Blending with Amphiphilic Block Copolymer

Solutions of Medhesive polymers dissolved in either methanol or chloroform were blended with a solution of 4-arm PEG-PLA-MA block copolymer (combined polymer concentration of 100 mg/ml) and cast on to bovine pericardium as the backing material, and then allowed to dry slowly. Before forming the adhesive joint, a dilute solution aqueous of sodium periodate (NaIO$_4$, 20 mg/ml) was added to the pericardium substrate to oxidize the adhesives and lap shear testing was performed following ASTM F2255 protocols. Adhesive properties of adhesive blends are summarized in Tables 13 and 14 using bovine pericardium and bone tissue as the test substrates, respectively. Increased content of the block copolymer increased the adhesive properties.

TABLE 13

Lap shear adhesion test results for adhesive blends of Medhesive-054 using bovine pericardium as the test substrate

| Weight % 4-arm PEG-PLA | Maximum Adhesive Strength (kPa) | Strain at Failure | Work of Adhesion (J/m$^2$) |
|---|---|---|---|
| 0 | 37.9 ± 11.5 | 0.42 ± 0.050 | 94.4 ± 42.2 |
| 5 | 101 ± 39.1 | 0.50 ± 0.10 | 173 ± 64.7 |
| 10 | 96.2 ± 58.6 | 0.48 ± 0.12 | 177 ± 74.5 |
| 20 | 137 ± 54.2 | 0.55 ± 0.060 | 267 ± 86.3 |

* Coated at 90 g/m$^2$

TABLE 14

Lap shear adhesion test results for adhesive blends of Medhesive-054 using bone tissue as the test substrate

| Coating Density (g/m$^2$) | Weight % 4-arm PEG-PLA | Maximum Adhesive Strength (kPa) | Strain at Failure | Work of Adhesion (J/m$^2$) |
|---|---|---|---|---|
| 60 | 0 | 50.3 ± 15.9 | 0.53 ± 0.11 | 110 ± 21.0 |
| 60 | 20 | 62.6 ± 7.76 | 0.59 ± 0.18 | 121 ± 28.2 |
| 90 | 20 | 91.5 ± 18.4 | 0.40 ± 0.050 | 134 ± 32.1 |

Multi-Layered Adhesive Coating

Figure 21:
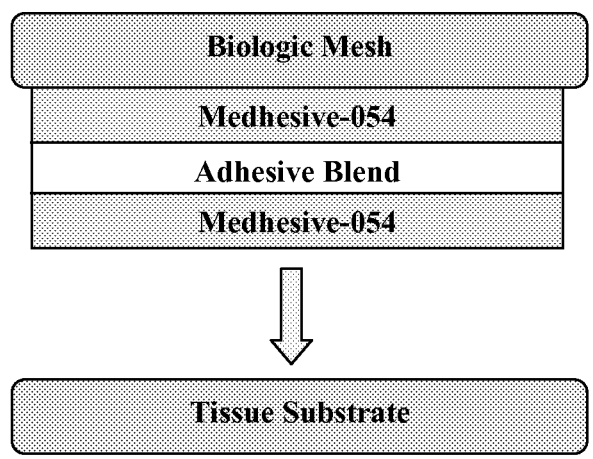
FIG. 21 represents a schematic of multi-layer adhesive films.

Multi-layer coating (FIG. 21) was achieved through successive solvent casting of Medheisve polymer solutions (dissolved in either methanol or chloroform) on to bovine pericardium as the backing followed by drying in vacuum. Lap shear adhesion tests (ASTM F2255) performed on trilayered adhesive coating is shown in Table 15 using bovine pericardium as the test substrate. The multilayer films consist of a 30 g/m$^2$ of Medhesive-112 (blended with 0-20 wt % with a 4-arm PEG-PLA-MA block copolymer) mid-layer sandwiched in between two 15 g/m$^2$ Medhesive-054 outer layers.

TABLE 15

Lap shear adhesion test results for multilayered adhesive film using bovine pericardium as the test substrate

| Weight % 4-arm PEG-PLA in mid-layer | Maximum Adhesive Strength (kPa) | Strain at Failure | Work of Adhesion (J/m²) |
|---|---|---|---|
| 0 | 184 ± 47.4 | 0.77 ± 0.28 | 499 ± 196 |
| 5 | 154 ± 42.7 | 0.73 ± 0.34 | 423 ± 95.5 |
| 20 | 190 ± 45.4 | 0.95 ± 0.21 | 576 ± 130 |

Multi-Layered Adhesive Coating

Figure 22:
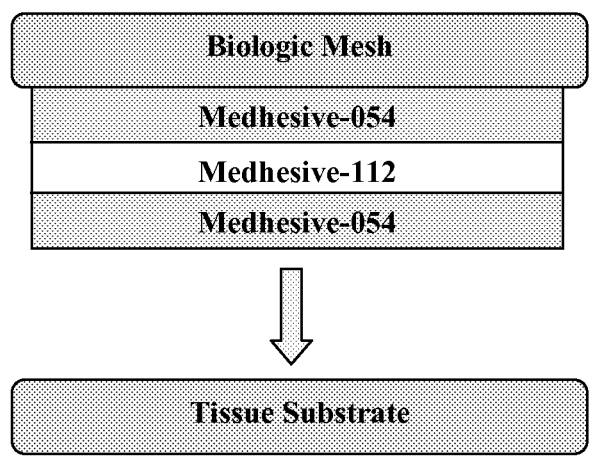
FIG. 22 represents another schematic of multi-layer adhesive films.

Multi-layer coating was achieved through successive solvent castings of Medhesive polymer solutions (dissolved in either methanol or chloroform) on to bovine pericardium followed by drying in vacuum. Lap shear adhesion tests (ASTM F2255) performed on trilayered adhesive coating is shown in Table 16 using bovine pericardium as the test substrate. Trilayer-1 consists of a 30 g/m² Medhesive-112 middle layer sandwiched in between two 15 g/m² Medhesive-054 outer layers while Trilayer-2 consists of a 60 g/m² Medhesive-112 middle layer sandwiched in between two 15 g/m² Medhesive-054 outer layers (See FIG. 22). These trilayered adhesives exhibited significantly improved adhesive properties as compared to a single layer of either Medhesive-054 or Medhesive-112. Performance of trilayer films on pieces of bone tissue cut from the scapula is shown in Table 17. Trilayer-3 consists of a 30 g/m² Medhesive-116 middle layer sandwiched in between two 15 g/m² Medhesive-054 outer layers while Trilayer-4 consists of a 60 g/m² Medhesive-116 middle layer sandwiched in between two 15 g/m² Medhesive-054 outer layers.

TABLE 16

Lap shear adhesion test results for trilayered adhesive coating using bovine pericardium as the test substrate

| Adhesive Formulation | Maximum Adhesive Strength (kPa) | Strain at Failure | Work of Adhesion (J/m²) |
|---|---|---|---|
| Trilayer-1 | 185 ± 47.4 | 0.62 ± 0.19 | 499 ± 196 |
| Trilayer-2 | 144 ± 23.9 | 0.68 ± 0.19 | 400 ± 81.3 |
| Medhesive-054* | 39.0 ± 12.5 | 0.39 ± 0.070 | 71.6 ± 16.3 |
| Medhesive-112* | 8.48 ± 4.64 | 0.46 ± 0.26 | 18.6 ± 9.96 |

*Coated at 90 g/m²

TABLE 17

Lap shear adhesion test results for trilayered adhesive coating using bone tissue as the test substrate

| Adhesive Formulation | Maximum Adhesive Strength (kPa) | Strain at Failure | Work of Adhesion (J/m²) |
|---|---|---|---|
| Trilayer-3 | 38.4 ± 21.4 | 0.34 ± 0.14 | 61.2 ± 44.1 |
| Trilayer-4 | 35.9 ± 14.1 | 0.52 ± 0.13 | 103 ± 53.0 |
| Medhesive-054* | 50.2 ± 15.9 | 0.53 ± 0.11 | 110 ± 21.0 |

*Coated at 60 g/m²

Adhesive-Coated on Biotape™

A polymer solution of Medhesive (dissolved in either methanol or chloroform) was coated on a fluorinated release liner using the solvent casting method and dried with vacuum. The dried adhesive film was pressed against Biotape™ (Wright Medical Technology, Inc.), an acellular porcine matrix, and incubated at 55° C. for 1 hour. The bioadhesive construct was tested using lap shear adhesion test (ASTM F2255) using bovine pericardium as the test substrate. Maximum lap shear strength and work of adhesion were found to be 125±16.9 kPa and 269±64.6 J/m², respectively, for Medhesive-096 coated at 240 g/m². A trilayer adhesive coating consist of a 30 g/m² Medhesive-112 (blended with 20 wt % 4-arm PEG-PLA-MA) middle layer sandwiched in between two 15 g/m² Medhesive-054 outer layers demonstrated maximum lap shear strength and work of adhesion were found to be 79.3±9.18 kPa and 216±80.9 J/m², respectively.

Tensile Testing of Adhesive Polymers

Medhesive polymers were cast into thin-films (70 mg/ml in chloroform) as previously described and their tensile mechanical properties were tested following ASTM standard D638 protocols. Tensile tests on dog-bone shaped films (9.53-mm gauge length, 3.80-mm gauge width, and 12.7-mm fillet radius, swollen in phosphate buffered saline (PBS) (pH 7.4) for 1 hr) were performed, and the maximal tensile strength was measured (Table 18). Both the Young's modulus and toughness were also determined, based on the initial slope and the area under the stress-strain curve, respectively.

TABLE 18

Tensile properties of polymer films

| Adhesive Formulation | Young's Modulus (kPa) | Maximum Strength (kPa) | Strain at Failure | Toughness (J/m²) |
|---|---|---|---|---|
| Medhesive-112 | 379 ± 53.9 | 449 ± 253 | 1.98 ± 1.31 | 716 ± 701 |
| Medhesive-116 | 479 ± 122 | 482 ± 122 | 1.40 ± 0.367 | 305 ± 111 |

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A compound comprising the formula (I)

(I)

-continued

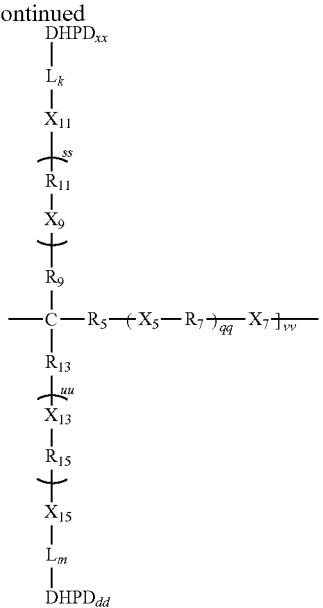

wherein
each $L_a$, $L_c$, $L_e$, $L_g$ and $L_i$, independently, is a linker;
each $L_k$ and $L_m$, independently, is a linker or a suitable linking group selected from amine, amide, ether, ester, urea, carbonate or urethane linking groups;
each X, $X_3$, $X_5$, $X_7$, $X_9$, $X_{11}$, $X_{13}$ and $X_{15}$, independently, is an oxygen atom or NR;
R, if present, is H or a branched or unbranched C1-10 alkyl group;
each $R_1$, $R_3$, $R_5$, $R_7$, $R_9$, $R_{11}$, $R_{13}$ and $R_{15}$, independently, is a branched or unbranched C1-C15 alkyl group;
each $DHPD_{xx}$ and $DHPD_{dd}$, independently, is a multihydroxy phenyl derivative residue;
ee is a value from 1 to about 80;
gg is a value from 0 to about 80;
ii is a value from 0 to about 80;
kk is a value from 0 to about 80;
mm is a value from 0 to about 80;
oo is a value from 1 to about 120;
qq is a value from 1 to about 120;
ss is a value from 1 to about 120;
uu is a value from 1 to about 120; and
vv is a value from 1 to about 80.

2. The compound of claim 1, wherein $L_a$ is a residue of a C1-C15, alkyl anhydride or activated dicarbonyl moiety, a poly(ethyleneglycol) bis(carboxymethyl)ether, polyethylene glycol or an amino acid.

3. The compound of claim 2, wherein the dicarbonyl moiety is a residue of succinic acid or the amino acid is glycine.

4. The compound of claim 1, wherein $L_c$ is a residue of a C1-C15 alkyl lactone or lactam, a poly C1-C15 alkyl lactone or lactam, a polyester, or a compound comprising the formula $Y_4$—$R_{17}$—C(=O)—$Y_6$,
wherein $Y_4$ is OH, NHR, a halide, or an activated derivative of OH or NHR;
$R_{17}$ is a branched or unbranched C1-C15 alkyl group; and
$Y_6$ is NHR, a halide, or OR.

5. The compound of claim 4, wherein the polylactone is a polycaprolactone.

6. The compound of claim 1, wherein $L_e$ is a residue of an alkylene diol, an alkylene diamine or a poly(alkylene oxide) polyether or derivative thereof.

7. The compound of claim 6, wherein $L_e$ is a poly(alkylene oxide) or —O—$CH_2CH_2$—O—$CH_2CH_2$—O—.

8. The compound of claim 1, wherein $L_g$ or $L_c$ is a residue of a C1-C15 alkyl lactone or lactam, a poly C1-C15 alkyl lactone or lactam, or a compound comprising the formula $Y_4$—$R_{17}$—C(=O)—$Y_6$,
wherein $Y_4$ is OH, NHR, a halide, or an activated derivative of OH or NHR;
$R_{17}$ is a branched or unbranched C1-C15 alkyl group; and
$Y_6$ is NHR, a halide, or OR.

9. The compound of claim 8, wherein the polylactone is polycaprolactone.

10. The compound of claim 1, wherein $L_i$ is a residue of a C1-C15 alkyl anhydride or activated dicarbonyl moiety, a poly(ethyleneglycol) bis(carboxymethyl)ether or an amino acid.

11. The compound of claim 10, wherein $L_i$ is a residue of succinic acid or glycine.

12. The compound of claim 1, wherein X, $X_7$, $X_{11}$ and $X_{15}$ are each O or NH.

13. The compound of claim 1, wherein $R_1$, $R_7$, $R_{11}$ and $R_{15}$ are each —$CH_2CH_2$—.

14. The compound of claim 1, wherein $X_3$, $X_5$, $X_9$ and $X_{13}$ are each O.

15. The compound of claim 1, wherein $R_3$, $R_5$, $R_9$ and $R_{13}$ are each —$CH_2$—.

16. The compound of claim 1, wherein $L_k$ and $L_m$ form an amide, ester or carbamate.

17. The compound of claim 1, wherein each $DHPD_{xx}$ and $DHPD_{dd}$, independently, is a residue of a formula comprising:

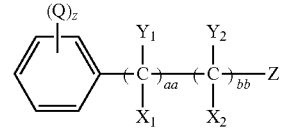

wherein Q is an OH;
"z" is 2 to 5;
each $X_1$, independently, is H, $NH_2$, OH, or COOH;
each $Y_1$, independently, is H, $NH_2$, OH, or COOH;
each $X_2$, independently, is H, $NH_2$, OH, or COOH;
each $Y_2$, independently, is H, $NH_2$, OH, or COOH;
Z is COOH, $NH_2$, OH or SH;
aa is a value of 0 to about 4;
bb is a value of 0 to about 4; and
optionally provided that when one of the combinations of $X_1$ and $X_2$, $Y_1$ and $Y_2$, $X_1$ and $Y_2$ or $Y_1$ and $X_2$ are absent, then a double bond is formed between the $C_{aa}$ and $C_{bb}$, further provided that aa and bb are each at least 1 to form the double bond when present.

18. The compound of claim 1, wherein $DHPD_{xx}$ and $DHPD_{dd}$ residues are from 3,4-dihydroxy phenylalanine (DOPA), 3,4-dihydroxyphenethylamine (dopamine), 3,4-dihydroxyhydrocinnamic acid (DOHA), 3,4-dihydroxyphenyl ethanol, 3,4 dihydroxyphenylacetic acid, 3,4 dihydroxyphenylamine, or 3,4-dihydroxybenzoic acid.

19. The compound of claim 1, wherein
$L_a$ is a residue of succinic acid;
$L_c$ is a residue of a polycaprolactone, a caprolactone, a polylactic acid, a polylactone or a lactic acid or lactone;
$L_e$ is a residue of a polyethylene glycol;
$L_g$ is a residue of a polycaprolactone, a caprolactone, a polylactic acid, a polylactone or a lactic acid or lactone;

$L_i$ is a residue of succinic anhydride;

$X, X_7, X_{11}$ and $X_{15}$ are each O or NH;

$R_1, R_7, R_{11}$ and $R_{15}$ are each —CH$_2$CH$_2$—;

$X_3, X_5, X_9$ and $X_{13}$ are each O;

$R_3, R_5, R_9$ and $R_{13}$ are each —CH$_2$—;

$L_k$ and $L_m$ form an amide; and $DHPD_{xx}$ and $DHPD_{dd}$ are residues from 3,4-dihydroxyhydrocinnamic acid (DOHA).

20. The compound of claim 1, wherein $L_a$ is a residue of glycine;

$L_c$ is a residue of a polycaprolactone, a caprolactone, a polylactic acid, a polylactone or a lactic acid or lactone;

$L_e$ is a residue of a polyethylene glycol;

$L_g$ is a residue of a polycaprolactone, a caprolactone, a polylactic acid, a polylactone or a lactic acid or lactone;

$L_i$ is a residue of glycine;

$X, X_7, X_{11}$ and $X_{15}$ are each O or NH;

$R_1, R_7, R_{11}$ and $R_{15}$ are each —CH$_2$CH$_2$—;

$X_3, X_5, X_9$ and $X_{13}$ are each O;

$R_3, R_5, R_9$ and $R_{13}$ are each —CH$_2$—;

$L_k$ and $L_m$ form a carbamate; and $DHPD_{xx}$ and $DHPD_{dd}$ are residues from 3,4 dihydroxyphenylethylamine.

21. The compound of claim 1, wherein $L_a$ is a residue of a poly(ethyleneglycol) bis(carboxymethyl)ether;

$L_c, L_e, L_g,$ and L, are absent;

ee is a value from 1 to about 11;

gg, ii, kk, and mm are each independently 0;

$X, X_7, X_{11}$ and $X_{15}$ are each O or NH;

$R_1, R_7, R_{11}$ and $R_{15}$ are each —CH$_2$CH$_2$—;

$X_3, X_5, X_9$ and $X_{13}$ are each O;

$R_3, R_5, R_9$ and $R_{13}$ are each —CH$_2$—;

$L_k$ and $L_m$ form an amide; and $DHPD_{xx}$ and $DHPD_{dd}$ are residues from 3,4-dihydroxyhydrocinnamic acid (DOHA).

22. A bioadhesive construct, comprising:

a support suitable for tissue repair or reconstruction; and a coating comprising a multihydroxyphenyl (DHPD) functionalized polymer (DHPp) of claim 1.

23. The bioadhesive construct of claim 22, further comprising an oxidant.

24. The bioadhesive construct of claim 22, wherein the oxidant is formulated with the coating.

25. The bioadhesive construct of claim 22, wherein the oxidant is applied to the coating.

26. The bioadhesive construct of claim 22, wherein the support is a film, a mesh, a membrane, a nonwoven or a prosthetic.

27. A blend of a polymer and a compound of claim 1.

28. The blend of claim 27, wherein the polymer is present in a range of about 1 to about 50 percent by weight.

29. The blend of claim 28, wherein the polymer is present in a range of about 1 to about 30 percent by weight.

30. A bioahesive construct comprising:

a support suitable for tissue repair or reconstruction; and a coating comprising the blend of claim 27.

31. The bioadhesive construct of claim 30, further comprising an oxidant.

32. The bioadhesive construct of claim 30, wherein the oxidant is formulated with the coating.

33. The bioadhesive construct of claim 30, wherein the oxidant is applied to the coating.

34. The bioadhesive construct of claim 30, wherein the support is a film, a mesh, a membrane, a nonwoven or a prosthetic.

35. A bioadhesive construct comprising:

a support suitable for tissue repair or reconstruction;

a first coating comprising a multihydroxyphenyl (DHPD) functionalized polymer (DHPp) of claim 1 and a polymer; and a second coating coated onto the first coating, wherein the second coating comprises a multihydroxyphenyl (DHPD) functionalized polymer (DHPp) of claim 1.

36. A bioadhesive construct comprising:

a support suitable for tissue repair or reconstruction;

a first coating comprising a first multihydroxyphenyl (DHPD) functionalized polymer (DHPp) of claim 1 and a first polymer; and a second coating coated onto the first coating, wherein the second coating comprises a second multihydroxyphenyl (DHPD) functionalized polymer (DHPp) of claim 1 and a second polymer, wherein the first and second polymer may be the same or different and wherein the first and second DHPp can be the same or different.

37. A bioadhesive construct comprising:

a support suitable for tissue repair or reconstruction;

a first coating comprising a first multihydroxyphenyl (DHPD) functionalized polymer (DHPp) of claim 1; and a second coating coated onto the first coating, wherein the second coating comprises a second multihydroxyphenyl (DHPD) functionalized polymer (DHPp) of claim 1, wherein the first and second DHPp can be the same or different.

38. The compound of claim 20, wherein $L_c$ is a residue of a polycaprolactone and $L_g$ is a residue of a polycaprolactone.

* * * * *